United States Patent
Hunter et al.

(10) Patent No.: US 11,928,834 B2
(45) Date of Patent: Mar. 12, 2024

(54) SYSTEMS AND METHODS FOR GENERATING THREE-DIMENSIONAL MEASUREMENTS USING ENDOSCOPIC VIDEO DATA

(71) Applicant: Stryker Corporation, Kalamazoo, MI (US)

(72) Inventors: Cole Kincaid Hunter, Santa Clara, CA (US); Brian Fouts, Morgan Hill, CA (US); Sanskruti Maske, Gondia (IN)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/664,640

(22) Filed: May 23, 2022

(65) Prior Publication Data
US 2022/0375114 A1      Nov. 24, 2022

Related U.S. Application Data

(60) Provisional application No. 63/264,650, filed on Nov. 29, 2021, provisional application No. 63/192,506, filed on May 24, 2021.

(51) Int. Cl.
*G06T 7/60* (2017.01)
*A61B 1/00* (2006.01)
(Continued)

(52) U.S. Cl.
CPC .......... *G06T 7/60* (2013.01); *A61B 1/000094* (2022.02); *A61B 34/10* (2016.02);
(Continued)

(58) Field of Classification Search
CPC ... G06T 7/60; G06T 7/11; G06T 7/593; G06T 17/00; G06T 2200/24; G06T 2207/10012;
(Continued)

(56) References Cited

U.S. PATENT DOCUMENTS 6,135,946 A * 10/2000 Konen ................... A61B 90/36
                                                                600/407
8,388,539 B2    3/2013 Yamamoto et al.
(Continued)

FOREIGN PATENT DOCUMENTS

CN          106327587 B      6/2019
CN          112184653 A *    1/2021    .............. G06T 5/30
(Continued)

OTHER PUBLICATIONS

Widya, Aji Resindra, et al. "3D reconstruction of whole stomach from endoscope video using structure-from-motion." 2019 41st Annual International Conference of the IEEE Engineering in Medicine and Biology Society (EMBC). IEEE, 2019 (Year: 2019).*
(Continued)

*Primary Examiner* — Maurice L. McDowell, Jr.
(74) *Attorney, Agent, or Firm* — Morrison & Foerster LLP

(57) ABSTRACT

Presented herein are systems and methods for performing three-dimensional measurements of a surgical space using two-dimensional endoscopic images. According to an aspect, video data taken from an endoscopic imaging device can be used to generate a three-dimensional model of the surgical space represented by the video data. In one or more examples, two-dimensional images from the video data can be used to generate a three-dimensional model of the surgical space. In one or more examples, the one or more two-dimensional images of the surgical space can include a fiducial marker as part of the image. Using both the depth information and a size reference provided by the fiducial marker, the systems and methods herein can generate a three-dimensional model of the surgical space. The generated three-dimensional model can then be used to perform a
(Continued)

variety of three-dimensional measurements in a surgical cavity in an accurate and efficient manner.

36 Claims, 20 Drawing Sheets

(51) Int. Cl.
| | |
|---|---|
| *A61B 34/10* | (2016.01) |
| *G01S 17/894* | (2020.01) |
| *G06T 7/11* | (2017.01) |
| *G06T 7/593* | (2017.01) |
| *G06T 17/00* | (2006.01) |

(52) U.S. Cl.
CPC .............. *G01S 17/894* (2020.01); *G06T 7/11* (2017.01); *G06T 7/593* (2017.01); *G06T 17/00* (2013.01); *A61B 2034/105* (2016.02); *G06T 2200/24* (2013.01); *G06T 2207/10012* (2013.01); *G06T 2207/10016* (2013.01); *G06T 2207/10068* (2013.01); *G06T 2207/20081* (2013.01)

(58) Field of Classification Search
CPC . G06T 2207/10016; G06T 2207/10068; G06T 2207/20081; G06T 2207/30204; G06T 7/579; G06T 7/62; A61B 1/000094; A61B 34/10; A61B 2034/105; G01S 17/894
See application file for complete search history.

(56) References Cited

U.S. PATENT DOCUMENTS

| | | | |
|---|---|---|---|
| 8,473,031 B2 | 6/2013 | Nixon et al. | |
| 8,911,358 B2 | 12/2014 | Koninckx et al. | |
| 9,105,092 B2 | 8/2015 | Lee et al. | |
| 9,367,928 B2 | 6/2016 | De Almeida Barreto et al. | |
| 9,433,390 B2 | 9/2016 | Nathaniel et al. | |
| 9,438,897 B2 | 9/2016 | Barreto et al. | |
| 9,492,240 B2 | 11/2016 | Itkowitz et al. | |
| 9,603,668 B2 | 3/2017 | Weingarten et al. | |
| 9,736,464 B2 | 8/2017 | Takao et al. | |
| 10,499,996 B2 | 12/2019 | De Almeida Barreto | |
| 10,504,239 B2 | 12/2019 | Rodrigues et al. | |
| 10,730,187 B2 | 8/2020 | Larkin et al. | |
| 10,796,499 B2 | 10/2020 | De Almeida Barreto et al. | |
| 11,335,075 B2 | 5/2022 | De Almeida Barreto et al. | |
| 11,388,310 B2 | 7/2022 | Mendonça Da Silva Gonçalves et al. | |
| 2007/0161854 A1* | 7/2007 | Alamaro ............ A61B 1/00194 600/109 | |
| 2007/0236514 A1 | 10/2007 | Agusanto et al. | |
| 2009/0005640 A1* | 1/2009 | Fehre .................. H04N 23/698 600/109 | |
| 2014/0078138 A1* | 3/2014 | Martin ................. A61B 8/0841 345/420 | |
| 2015/0237325 A1 | 8/2015 | Angot et al. | |
| 2016/0199147 A1 | 7/2016 | Shin | |
| 2017/0084036 A1 | 3/2017 | Pheiffer et al. | |
| 2019/0110855 A1 | 4/2019 | Barral et al. | |
| 2019/0320878 A1 | 10/2019 | Duindam et al. | |
| 2021/0113280 A1* | 4/2021 | Ummalaneni ....... A61B 6/0487 |
| 2022/0313364 A1 | 10/2022 | Dubois et al. |
| 2022/0354356 A1* | 11/2022 | Weeks .................. G06T 7/0012 |
| 2022/0375173 A1* | 11/2022 | Zang ...................... G06T 7/344 |
| 2022/0383588 A1 | 12/2022 | De Almeida Barreto et al. |
| 2022/0392110 A1 | 12/2022 | De Almeida Barreto et al. |
| 2022/0406025 A1 | 12/2022 | De Almeida Barreto et al. |
| 2023/0190136 A1* | 6/2023 | Kumar ................. A61B 5/1076 600/587 |

FOREIGN PATENT DOCUMENTS

| | | | |
|---|---|---|---|
| WO | WO-2010061293 A2 * | 6/2010 | ......... A61B 1/00057 |
| WO | 2015136537 A2 | 9/2015 | |
| WO | WO-2017053505 A2 * | 3/2017 | ............. F01D 17/20 |
| WO | WO-2017155131 A1 * | 9/2017 | ......... A61B 1/00087 |
| WO | 2019164275 A1 | 8/2019 | |
| WO | 2021071988 A1 | 4/2021 | |
| WO | 2021071991 A1 | 4/2021 | |
| WO | 2021211524 A1 | 10/2021 | |
| WO | 2021211603 A1 | 10/2021 | |
| WO | 2021263174 A1 | 12/2021 | |
| WO | 2022229816 A1 | 11/2022 | |
| WO | 2023034194 A1 | 3/2023 | |
| WO | 2023044507 A1 | 3/2023 | |

OTHER PUBLICATIONS

Fu et al. (2021). "The Future of Endoscopic Navigation: A Review of Advanced Endoscopic Vision Technology," IEEE Access 9: 41144-41167.

Huang et al. (2020). "Tracking and visualization of the sensing area for a tethered laparoscopic gamma probe," International Journal of Computer Assisted Radiology and Surgery 15, 1389-1397.

International Search Report and Written Opinion dated Nov. 21, 2022, directed to International Application No. PCT/US2022/072512; 20 pages.

Leonard et al., (2016). "Image-Based Navigation for Functional Endoscopic Sinus Surgery Using Structure From Motion," Proc SPIE Int Soc Opt Eng.; 14 pages.

Lin et al. (2015). "Video-based 3D reconstruction, laparoscope localization and deformation recovery for abdominal minimally invasive surgery: a survey," The International Journal of Medical Robotics and Computer Assisted Surgery, 12(2): 158-178.

Mahmoud et al., (2016). "ORBSLAM-based Endoscope Tracking and 3D Reconstruction," Cornell University Library; 13 pages.

Nagle-McNaughton et al. (2020). "Measuring Change Using Quantitative Differencing of Repeat Structure-From- Motion Photogrammetry: The Effect of Storms on Coastal Boulder Deposits," Remote Sensing. 12(42); 27 pages.

Raposo et al., "Video-Based Computer Aided Arthroscopy for Patient Specific Reconstruction of the Anterior Cruciate Ligament," 18th International Conference on Medical Image Computing and Computer-Assisted Intervention, Sep. 13, 2018, Granada, Spain, 125-133.

Terabayashi et al. (2009). "Measurement of Three-Dimensional Environment with a Fish-Eye Camera Based on Structure from Motion-Error Analysis," Journal of Robotics and Mechatronics 21(6): 680-688.

* cited by examiner

SYSTEMS AND METHODS FOR GENERATING THREE-DIMENSIONAL MEASUREMENTS USING ENDOSCOPIC VIDEO DATA

CROSS-REFERENCE TO RELATED APPLICATIONS

This application claims the benefit of U.S. Provisional Application No. 63/192,506, filed May 24, 2021, and U.S. Provisional Application No. 63/264,650, filed Nov. 29, 2021, the entire contents of each of which are hereby incorporated by reference herein.

FIELD

This disclosure relates to generating three-dimensional measurements in a surgical space, e.g. during a minimally invasive surgical procedure, and more specifically, to using two-dimensional image data from an endoscopic imaging device to generate a three-dimensional model of the surgical space and using the three-dimensional model to take measurements in three dimensions.

BACKGROUND

Minimally invasive surgery generally involves the use of a high-definition camera coupled to an endoscope inserted, such as pre-inserted, into a patient to provide a surgeon with a clear and precise view within the body. In many surgical contexts, the surgeon is often required to make precise distance measurements within the surgical space so as to accurately perform a given procedure during the surgery. Prior methods of estimating measurements in a surgical space can include the use of hooked probes in the surgical cavity; however this method can be inaccurate and can be limited by the trajectory that the hooked probe can be positioned within the cavity. Other prior methods include connecting a piece of suture to an anchor, marking the suture with a sterile marker outside of the joint, draw the suture out across the anatomy, and mark the suture again. This method, while perhaps producing an accurate result, can be complex and time consuming for a surgeon to undertake during a surgical procedure.

Conventionally, the surgeon may estimate distances by viewing the video data supplied by an endoscopic device. Using the video data as well as the surgeon's general knowledge of the anatomy in the surgical space, the surgeon can estimate distances between two points in the surgical space. However, this "human" method of estimating distances can lead to inaccurate measurements. The primary source of inaccuracy with this method is that the surgeon is using a two-dimensional image provided by the video data of the endoscopic imaging device, to estimate a measurement that in reality is taking place in a three-dimensional space. Thus, the surgeon's estimate of distance may not take into account the differences in depth between the two points that the surgeon is measuring the distance between. An accurate distance measurement can require measurements in three dimensions, but the endoscopic device shows an image in two dimensions and thus the surgeon may not be accurately taking into account the changes in three dimensions between two points when estimating distance. In other words, the surgeon may be estimating distance using the changes in the vertical and horizontal positions between two points, however the surgeon may not be considering the changes in depth between two points when estimating the distance between two points. Because two-dimensional images lack depth perception, the surgeon may not be able to accurately measure the distances between two points because those measurements do not take into account any changes in depth between the two points.

Even assuming that an accurate representation of depth was not required to estimate distances between two points in a surgical space, the accuracy of any measurement may still be entirely reliant on the surgeon's ability to estimate distances based on the images they see provided by the endoscopic device. Surgeons can improve the accuracy of their measurements by placing measuring devices in the surgical space (such as a ruler) to measure the distance between two points. However, doing so requires the surgeon to place additional objects in the surgical space which is limited by the surgical portal location and trajectory.

Thus, providing the surgeon with a three-dimensional model of the surgical space and providing them with a way to measure distance without requiring dedicated measurement tools can improve the accuracy of the measurement without increasing the complexity of the surgery.

SUMMARY

According to an aspect, video data taken from an endoscopic imaging device can be used to generate a three-dimensional model of the surgical space represented by the video data. In one or more examples, the video data from the endoscopic imaging device can be used to generate one or more two-dimensional images of the surgical space. The two-dimensional images can be used to generate a three-dimensional model of the surgical space. For instance, in one or more examples, a structure-from-motion algorithm can be applied to the two-dimensional images so as to generate depth information about the image and then the depth information can be used to generate a three-dimensional model of the surgical space. Optionally, depth data about the surgical space can be collected using a time-of-flight sensor. Optionally, depth data about the surgical space can be collected using a stereo camera. In one or more examples, a fiducial marker can be inserted into the surgical space, and the one or more two-dimensional images of the surgical space can include the fiducial marker as part of the image. The fiducial marker can also be used to generate a three-dimensional model of the surgical space by providing a size reference within the surgical space. Using both the depth information and a size reference provided by the fiducial marker, the systems and methods herein can generate a three-dimensional model of the surgical space. In one or more examples, a distal end of a surgical device can be used as the fiducial marker in a surgical space.

In one or more examples, a method for measuring three-dimensional distances using endoscopic images comprises: receiving video data captured from an endoscopic imaging device configured to image an internal area of a patient, capturing one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both, generating a three-dimensional model of the internal area based on the captured one or more two-dimensional images, determining a size of a three-dimensional area of the three-dimensional model based on the one or more fiducial markers of the object configured to indicate the pre-determined dimension, identifying a first point on the one or more two-dimensional images, identifying a second point on the one or more two-dimensional images, and determining a three-dimensional measurement between the first point and the second point in the area based on the determined size of the three-dimensional area and the generated three-dimensional model of the area.

Optionally, capturing the one or more two-dimensional images comprises: in response to a user requesting a measurement, receiving a first indication to mark a start time point in the received video data; receiving a second indication to mark a stop time point in the received video data, extracting a first two-dimensional image corresponding to the first indication; and extracting a second two-dimensional image corresponding to the second indication.

Optionally, receiving the first and second indication comprises pushing a button located on the endoscopic imaging device.

Optionally, receiving the first and second indication comprises pushing a button on a device that is separate from the imaging device.

Optionally, capturing the one or more two-dimensional images comprises: receiving a first indication at a graphical user interface on a computing device display receiving a second indication at the graphical user interface on the computing device display, extracting a first two-dimensional image corresponding to the first indication; and extracting a second two-dimensional image corresponding to the second indication.

Optionally, capturing the one or more two-dimensional images comprises: capturing a first image with the endoscopic imaging device located at a first position in the area; and capturing a second image with the imaging device located at a second position in the area.

Optionally, generating a three-dimensional model of the area based on the captured one or more two-dimensional images comprises applying a structure-from-motion procedure to the first and second images to generate the three-dimensional model of the area.

Optionally, the method comprises determining whether the received video data includes enough motion of the imaging device to perform the structure-from-motion procedure.

Optionally, generating a three-dimensional model of the area based on the captured one or more two-dimensional images comprises: capturing a first two-dimensional image of the area; receiving data from a time-of-flight sensor, wherein the received data corresponds to the imaged area; and generating the three-dimensional model of the area based on the captured first two-dimensional image of the area and the received data from the time-of-flight sensor.

Optionally, the endoscopic imaging device comprises a stereo camera, and wherein capturing the one or more two-dimensional images comprises capturing a first two-dimensional image and a second two-dimensional image using the stereo camera of the endoscopic imaging device.

Optionally, generating a three-dimensional model of the area based on the captured one or more two-dimensional images comprises applying a structure-from-motion procedure to the first and second two-dimensional images to generate the three-dimensional model of the area.

Optionally, the method comprises determining whether the received video data includes enough motion of the imaging device to perform the structure-from-motion procedure.

Optionally, the one or more fiducial markers of the object comprise one or more barcodes configured to identify information pertaining to the size of the object.

Optionally, the one or more barcodes are configured to identify information pertaining to an orientation of the object.

Optionally, the one or more barcodes are configured to identify the object.

Optionally, the one or more fiducial markers of the object include a first marking on the object and a second marking on the object, and wherein a distance between the first marking and the second marking is pre-determined.

Optionally, the one or more fiducial markers of the object comprise one or more Quick Response (QR) codes configured to identify information pertaining to the size of the object.

Optionally, the one or more QR codes are configured to identify information pertaining to an orientation of the object.

Optionally, the one or more QR codes are configured to identify the object.

Optionally, identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

Optionally, segmenting the object from the first and second images of the one or more two-dimensional images comprises applying one or more machine learning models to the first and second images, wherein the one or more machine learning models are created using a supervised training process that comprises using one or more annotated images to train the machine learning model.

Optionally, the supervised training process comprises: applying one or more annotations to each image of a plurality of images to indicate one or more regions associated with the image; and processing each image of the plurality of images and its corresponding one or more annotations.

Optionally, the one or more machine learning models comprises an instrument identification machine learning model configured to generate one or more classification metrics associated with identifying one or more instruments in the received video data.

Optionally, the instrument identification machine learning model is trained using one or more training images annotated with a type of instrument pictured in the training image.

Optionally, the one or more machine learning models comprise one or more convolutional neural networks.

Optionally, identifying the first point on the one more two-dimensional images comprises identifying a position of an end of the object based on the segmented object from the first image of the one or more two-dimensional images, and wherein identifying the second point on the one or more two-dimensional images comprises identifying a position of an end of the object based on the segmented object from the second image of the one or more two-dimensional images.

Optionally, identifying the first and second points of the one or more two-dimensional images comprises: displaying a graphical user interface at a display of a computing device, wherein the graphical user interface includes a visualization of the imaged area; receiving a first input from a user at the graphical user interface; identifying the first point on the one or more two-dimensional images based on the received first user input; receiving a second input from the user at the graphical user interface; and identifying the second point on the one or more two-dimensional images based on the received second user input.

Optionally, determining a three-dimensional measurement between the first point and the second point in the area based on the determined size of the area and the generated three-dimensional model of the area comprises determining a distance along a surface between the first position and the second position.

Optionally, determining a three-dimensional measurement between the first point and the second point in the area based on the determined size of the area and the generated three-dimensional model of the area comprises determining the point-to-point distance between the first position and the second position.

Optionally, the method further comprises: defining a plane in the area based on the identified first and second points; and determining a three-dimensional area based on the defined plane.

Optionally, the method is performed on a computing device located in a surgical theater.

Optionally, the method is performed on a cloud-based computing device.

Optionally, the object is a pointing tool.

Optionally, the object is a drill guide.

Optionally, the object is a shaver.

Optionally, the object is a radio frequency (RF) probe.

Optionally, the object is an arthroscopic tool with a rigid component.

Optionally, the first point on the one or more two-dimensional images and the second-point on the one or more two dimensional images are located on a contour of an internal area patient to be grafted, and wherein the method comprises: transmitting the captured one or more two-dimensional images of the internal area from the received data to a projector, wherein the projector is configured to project the captured one or more two-dimensional images onto a graft positioned in a field of view of the projector; and transmitting the determined three-dimensional measurement between the first point and the second point in the area to the projector, wherein the projector is configured to scale the projected one or more two-dimensional images onto the graft positioned in the field of view of the projector based on the determined the determined three-dimensional measurement between the first point and the second point in the area.

Optionally, an internal area of the patient to be grafted comprises a section of cartilage of the patient.

Optionally, an internal area of the patient to be grafted comprises a vessel of the patient.

Optionally, an internal area of the patient to be grafted comprises a ligament of the patient.

Optionally, the first point on the one or more two-dimensional images is located on an end of a tool, the second-point on the one or more two dimensional images are located on an anatomical feature of the patient, and wherein the method comprises: comparing the determined three-dimensional measurement between the first point and the second point in the area to a pre-determined threshold; and transmitting a notification to a user if the determined three-dimensional measurement between the first point and the second point in the area is less than the pre-determined threshold Optionally, identifying the second point on the one or more two dimensional images comprises: identifying a fluoresced anatomical feature in the one or more captured two-dimensional images; and determining the contours of the fluoresced anatomical features using the generated three-dimensional model.

Optionally, identifying the second point on the one or more two dimensional images comprises: applying a machine learning classifier to the one or more captured two-dimensional images to determine the location of an anatomical feature within the one or more captured two-dimensional images, wherein the machine learning classifier is trained using a plurality of training images that comprise the anatomical feature fluoresced within the training image; and determining the contours of the anatomical feature using the generated three dimensional model.

Optionally, the anatomical features includes a nerve and/or blood vessel of the patient.

Optionally, determining a size of the three-dimensional area of the three-dimensional model based on the one or more fiducial markers of the object comprises applying one or more machine learning models to the captured one or more two-dimensional, wherein the one or more machine learning classifiers are configured to estimate a pose of the object.

Optionally, the estimated pose of the object generated by the one or more machine learning models are used to determine a ratio between an actual size of the object, and a size of the object in the image, and wherein determining the size of the three-dimensional area of the three-dimensional model is based on the determined ratio.

Optionally, identifying a first point on the one or more two-dimensional images comprises identifying a point on a first surgical tool visualized in the one or more two-dimensional images, wherein identifying a second point on the one or more two-dimensional images comprises identifying a point on a second surgical tool visualized in the one or more two-dimensional images, and wherein determining a three-dimensional measurement between the first point and the second point in the area based on the determined size of the three-dimensional area and the generated three-dimensional model of the area comprises determining a three-dimensional measurement between the identified point on the first surgical tool and the identified point on the second surgical tool.

Optionally, the one or more fiducial markers of the object comprise one or more ArUco markers configured to identify information pertaining to the size of the object.

Optionally, the one or more ArUco markers comprise one or more bit patterns encoded with error correction.

Optionally, the one or more ArUco markers are square shaped.

Optionally, determining a size of a three-dimensional area of the three-dimensional model based on the one or more fiducial markers of the object configured to indicate the pre-determined dimension comprises: locating the one or more ArUco markers in the captured one or more two-dimensional images; and identifying the ArUco markers in the captured one or more two-dimensional images.

Optionally, identifying the ArUco markers in the captured one or more two-dimensional images comprises applying one or more computer vision processes to the captured one or more two-dimensional images.

Optionally, the one or more computer vision processes are calibrated using a calibration device, wherein the calibration devices comprises: a chamber, wherein the chamber is configured to be filled with a liquid; one or more test ArUco markers, wherein the test ArUco markers are disposed within the chamber; and an imaging device interface, wherein the imaging device interface is configured to receive an imaging device, and position the imaging device so that the imaging device can view the one or more test ArUco markers disposed within the chamber.

Optionally, calibrating the one or more computer vision processes comprises: generating one or more images of the one or more test ArUco markers within the chamber of the calibration device using an imaging device connected to the imaging device interface of the calibration device; and applying a correction factor to the one or more computer vision processes, wherein the correction factor is based on the generated one or more images.

Optionally, the one or more annotated images to train the machine learning model comprises synthetic training images.

In one or more examples, a system for measuring three-dimensional distances using endoscopic images comprises: a memory; one or more processors; wherein the memory stores one or more programs that when executed by the one or more processors, cause the one or more processors to: receive video data captured from an endoscopic imaging device configured to image an internal area of a patient; capture one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both; generate a three-dimensional model of the internal area based on the captured one or more two-dimensional images; determine a size of a three-dimensional area of the three-dimensional model based on the one or more fiducial markers of the object configured to indicate the pre-determined dimension; identify a first point on the one or more two-dimensional images; identify a second point on the one or more two-dimensional images; and determine a three-dimensional measurement between the first point and the second point in the area based on the determined size of the three-dimensional area and the generated three-dimensional model of the area.

Optionally, capturing the one or more two-dimensional images comprises: in response to a user requesting a measurement, receiving a first indication to mark a start time point in the received video data; receiving a second indication to mark a stop time point in the received video data, extracting a first two-dimensional image corresponding to the first indication; and extracting a second two-dimensional image corresponding to the second indication.

Optionally, receiving the first and second indication comprises pushing a button located on the endoscopic imaging device.

Optionally, receiving the first and second indication comprises pushing a button on a device that is separate from the imaging device.

Optionally, capturing the one or more two-dimensional images comprises: receiving a first indication at a graphical user interface on a computing device display receiving a second indication at the graphical user interface on the computing device display, extracting a first two-dimensional image corresponding to the first indication; and extracting a second two-dimensional image corresponding to the second indication.

Optionally, capturing the one or more two-dimensional images comprises: capturing a first image with the endoscopic imaging device located at a first position in the area; and capturing a second image with the imaging device located at a second position in the area.

Optionally, generating a three-dimensional model of the area based on the captured one or more two-dimensional images comprises applying a structure-from-motion procedure to the first and second images to generate the three-dimensional model of the area.

Optionally, the method comprises determining whether the received video data includes enough motion of the imaging device to perform the structure-from-motion procedure.

Optionally, generating a three-dimensional model of the area based on the captured one or more two-dimensional images comprises: capturing a first two-dimensional image of the area; receiving data from a time-of-flight sensor, wherein the received data corresponds to the imaged area; and generating the three-dimensional model of the area based on the captured first two-dimensional image of the area and the received data from the time-of-flight sensor.

Optionally, the endoscopic imaging device comprises a stereo camera, and wherein capturing the one or more two-dimensional images comprises capturing a first two-dimensional image and a second two-dimensional image using the stereo camera of the endoscopic imaging device.

Optionally, generating a three-dimensional model of the area based on the captured one or more two-dimensional images comprises applying a structure-from-motion procedure to the first and second two-dimensional images to generate the three-dimensional model of the area.

Optionally, the method comprises determining whether the received video data includes enough motion of the imaging device to perform the structure-from-motion procedure.

Optionally, the one or more fiducial markers of the object comprise one or more barcodes configured to identify information pertaining to the size of the object.

Optionally, the one or more barcodes are configured to identify information pertaining to an orientation of the object.

Optionally, the one or more barcodes are configured to identify the object.

Optionally, the one or more fiducial markers of the object include a first marking on the object and a second marking on the object, and wherein a distance between the first marking and the second marking is pre-determined.

Optionally, the one or more fiducial markers of the object comprise one or more Quick Response (QR) codes configured to identify information pertaining to the size of the object.

Optionally, the one or more QR codes are configured to identify information pertaining to an orientation of the object.

Optionally, the one or more QR codes are configured to identify the object.

Optionally, identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

Optionally, segmenting the object from the first and second images of the one or more two-dimensional images comprises applying one or more machine learning models to the first and second images, wherein the one or more machine learning models are created using a supervised training process that comprises using one or more annotated images to train the machine learning model.

Optionally, the supervised training process comprises: applying one or more annotations to each image of a plurality of images to indicate one or more regions associated with the image; and processing each image of the plurality of images and its corresponding one or more annotations.

Optionally, the one or more machine learning models comprises an instrument identification machine learning model configured to generate one or more classification metrics associated with identifying one or more instruments in the received video data.

Optionally, the instrument identification machine learning model is trained using one or more training images annotated with a type of instrument pictured in the training image.

Optionally, the one or more machine learning models comprise one or more convolutional neural networks.

Optionally, identifying the first point on the one more two-dimensional images comprises identifying a position of an end of the object based on the segmented object from the first image of the one or more two-dimensional images, and wherein identifying the second point on the one or more two-dimensional images comprises identifying a position of an end of the object based on the segmented object from the second image of the one or more two-dimensional images.

Optionally, identifying the first and second points of the one or more two-dimensional images comprises: displaying a graphical user interface at a display of a computing device, wherein the graphical user interface includes a visualization of the imaged area; receiving a first input from a user at the graphical user interface; identifying the first point on the one or more two-dimensional images based on the received first user input; receiving a second input from the user at the graphical user interface; and identifying the second point on the one or more two-dimensional images based on the received second user input.

Optionally, determining a three-dimensional measurement between the first point and the second point in the area based on the determined size of the area and the generated three-dimensional model of the area comprises determining a distance along a surface between the first position and the second position.

Optionally, determining a three-dimensional measurement between the first point and the second point in the area based on the determined size of the area and the generated three-dimensional model of the area comprises determining the point-to-point distance between the first position and the second position.

Optionally, the method further comprises: defining a plane in the area based on the identified first and second points; and determining a three-dimensional area based on the defined plane.

Optionally, the method is performed on a computing device located in a surgical theater.

Optionally, the method is performed on a cloud-based computing device.

Optionally, the object is a pointing tool.

Optionally, the object is a drill guide.

Optionally, the object is a shaver.

Optionally, the object is a radio frequency (RF) probe.

Optionally, the object is an arthroscopic tool with a rigid component.

Optionally, the first point on the one or more two-dimensional images and the second-point on the one or more two dimensional images are located on a contour of an internal area patient to be grafted, and wherein the method comprises: transmitting the captured one or more two-dimensional images of the internal area from the received data to a projector, wherein the projector is configured to project the captured one or more two-dimensional images onto a graft positioned in a field of view of the projector; and transmitting the determined three-dimensional measurement between the first point and the second point in the area to the projector, wherein the projector is configured to scale the projected one or more two-dimensional images onto the graft positioned in the field of view of the projector based on the determined the determined three-dimensional measurement between the first point and the second point in the area.

Optionally, an internal area of the patient to be grafted comprises a section of cartilage of the patient.

Optionally, an internal area of the patient to be grafted comprises a vessel of the patient.

Optionally, an internal area of the patient to be grafted comprises a ligament of the patient.

Optionally, the first point on the one or more two-dimensional images is located on an end of a tool, the second-point on the one or more two dimensional images are located on an anatomical feature of the patient, and wherein the method comprises: comparing the determined three-dimensional measurement between the first point and the second point in the area to a pre-determined threshold; and transmitting a notification to a user if the determined three-dimensional measurement between the first point and the second point in the area is less than the pre-determined threshold.

Optionally, identifying the second point on the one or more two dimensional images comprises: identifying a fluoresced anatomical feature in the one or more captured two-dimensional images; and determining the contours of the fluoresced anatomical features using the generated three-dimensional model.

Optionally, identifying the second point on the one or more two dimensional images comprises: applying a machine learning classifier to the one or more captured two-dimensional images to determine the location of an anatomical feature within the one or more captured two-dimensional images, wherein the machine learning classifier is trained using a plurality of training images that comprise the anatomical feature fluoresced within the training image; and determining the contours of the anatomical feature using the generated three dimensional model.

Optionally, the anatomical features includes a nerve and/or blood vessel of the patient.

Optionally, determining a size of the three-dimensional area of the three-dimensional model based on the one or more fiducial markers of the object comprises applying one or more machine learning models to the captured one or more two-dimensional, wherein the one or more machine learning classifiers are configured to estimate a pose of the object.

Optionally, the estimated pose of the object generated by the one or more machine learning models are used to determine a ratio between an actual size of the object, and a size of the object in the image, and wherein determining the size of the three-dimensional area of the three-dimensional model is based on the determined ratio.

Optionally, identifying a first point on the one or more two-dimensional images comprises identifying a point on a first surgical tool visualized in the one or more two-dimensional images, wherein identifying a second point on the one or more two-dimensional images comprises identifying a point on a second surgical tool visualized in the one or more two-dimensional images, and wherein determining a three-dimensional measurement between the first point and the second point in the area based on the determined size of the three-dimensional area and the generated three-dimensional model of the area comprises determining a three-dimensional measurement between the identified point on the first surgical tool and the identified point on the second surgical tool.

Optionally, the one or more fiducial markers of the object comprise one or more ArUco markers configured to identify information pertaining to the size of the object.

Optionally, the one or more ArUco markers comprise one or more bit patterns encoded with error correction.

Optionally, the one or more ArUco markers are square shaped.

Optionally, determining a size of a three-dimensional area of the three-dimensional model based on the one or more fiducial markers of the object configured to indicate the pre-determined dimension comprises: locating the one or more ArUco markers in the captured one or more two-dimensional images; and identifying the ArUco markers in the captured one or more two-dimensional images.

Optionally, identifying the ArUco markers in the captured one or more two-dimensional images comprises applying one or more computer vision processes to the captured one or more two-dimensional images.

Optionally, the one or more computer vision processes are calibrated using a calibration device, wherein the calibration devices comprises: a chamber, wherein the chamber is configured to be filled with a liquid; one or more test ArUco markers, wherein the test ArUco markers are disposed within the chamber; and an imaging device interface, wherein the imaging device interface is configured to receive an imaging device, and position the imaging device so that the imaging device can view the one or more test ArUco markers disposed within the chamber.

Optionally, calibrating the one or more computer vision processes comprises: generating one or more images of the one or more test ArUco markers within the chamber of the calibration device using an imaging device connected to the imaging device interface of the calibration device; and applying a correction factor to the one or more computer vision processes, wherein the correction factor is based on the generated one or more images.

Optionally, the one or more annotated images to train the machine learning model comprises synthetic training images.

In one or more examples, a non-transitory computer readable storage medium storing one or more programs for measuring three-dimensional distances, for execution by one or more processors of an electronic device that when executed by the device, causes the device to: receive video data captured from an endoscopic imaging device configured to image an internal area of a patient; capture one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both; generate a three-dimensional model of the internal area based on the captured one or more two-dimensional images; determine a size of a three-dimensional area of the three-dimensional model based on the one or more fiducial markers of the object configured to indicate the pre-determined dimension; identify a first point on the one or more two-dimensional images; identify a second point on the one or more two-dimensional images; and determine a three-dimensional measurement between the first point and the second point in the area based on the determined size of the three-dimensional area and the generated three-dimensional model of the area.

Optionally, capturing the one or more two-dimensional images comprises: in response to a user requesting a measurement, receiving a first indication to mark a start time point in the received video data; receiving a second indication to mark a stop time point in the received video data, extracting a first two-dimensional image corresponding to the first indication; and extracting a second two-dimensional image corresponding to the second indication.

Optionally, receiving the first and second indication comprises pushing a button located on the endoscopic imaging device.

Optionally, receiving the first and second indication comprises pushing a button on a device that is separate from the imaging device.

Optionally, capturing the one or more two-dimensional images comprises: receiving a first indication at a graphical user interface on a computing device display receiving a second indication at the graphical user interface on the computing device display, extracting a first two-dimensional image corresponding to the first indication; and extracting a second two-dimensional image corresponding to the second indication.

Optionally, capturing the one or more two-dimensional images comprises: capturing a first image with the endoscopic imaging device located at a first position in the area; and capturing a second image with the imaging device located at a second position in the area.

Optionally, generating a three-dimensional model of the area based on the captured one or more two-dimensional images comprises applying a structure-from-motion procedure to the first and second images to generate the three-dimensional model of the area.

Optionally, the method comprises determining whether the received video data includes enough motion of the imaging device to perform the structure-from-motion procedure.

Optionally, generating a three-dimensional model of the area based on the captured one or more two-dimensional images comprises: capturing a first two-dimensional image of the area; receiving data from a time-of-flight sensor, wherein the received data corresponds to the imaged area; and generating the three-dimensional model of the area based on the captured first two-dimensional image of the area and the received data from the time-of-flight sensor.

Optionally, the endoscopic imaging device comprises a stereo camera, and wherein capturing the one or more two-dimensional images comprises capturing a first two-dimensional image and a second two-dimensional image using the stereo camera of the endoscopic imaging device.

Optionally, generating a three-dimensional model of the area based on the captured one or more two-dimensional images comprises applying a structure-from-motion procedure to the first and second two-dimensional images to generate the three-dimensional model of the area.

Optionally, the method comprises determining whether the received video data includes enough motion of the imaging device to perform the structure-from-motion procedure.

Optionally, the one or more fiducial markers of the object comprise one or more barcodes configured to identify information pertaining to the size of the object.

Optionally, the one or more barcodes are configured to identify information pertaining to an orientation of the object.

Optionally, the one or more barcodes are configured to identify the object.

Optionally, the one or more fiducial markers of the object include a first marking on the object and a second marking on the object, and wherein a distance between the first marking and the second marking is pre-determined.

Optionally, the one or more fiducial markers of the object comprise one or more Quick Response (QR) codes configured to identify information pertaining to the size of the object.

Optionally, the one or more QR codes are configured to identify information pertaining to an orientation of the object.

Optionally, the one or more QR codes are configured to identify the object.

Optionally, identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

Optionally, segmenting the object from the first and second images of the one or more two-dimensional images comprises applying one or more machine learning models to the first and second images, wherein the one or more machine learning models are created using a supervised training process that comprises using one or more annotated images to train the machine learning model.

Optionally, the supervised training process comprises: applying one or more annotations to each image of a plurality of images to indicate one or more regions associated with the image; and processing each image of the plurality of images and its corresponding one or more annotations.

Optionally, the one or more machine learning models comprises an instrument identification machine learning model configured to generate one or more classification metrics associated with identifying one or more instruments in the received video data.

Optionally, the instrument identification machine learning model is trained using one or more training images annotated with a type of instrument pictured in the training image.

Optionally, the one or more machine learning models comprise one or more convolutional neural networks.

Optionally, identifying the first point on the one more two-dimensional images comprises identifying a position of an end of the object based on the segmented object from the first image of the one or more two-dimensional images, and wherein identifying the second point on the one or more two-dimensional images comprises identifying a position of an end of the object based on the segmented object from the second image of the one or more two-dimensional images.

Optionally, identifying the first and second points of the one or more two-dimensional images comprises: displaying a graphical user interface at a display of a computing device, wherein the graphical user interface includes a visualization of the imaged area; receiving a first input from a user at the graphical user interface; identifying the first point on the one or more two-dimensional images based on the received first user input; receiving a second input from the user at the graphical user interface; and identifying the second point on the one or more two-dimensional images based on the received second user input.

Optionally, determining a three-dimensional measurement between the first point and the second point in the area based on the determined size of the area and the generated three-dimensional model of the area comprises determining a distance along a surface between the first position and the second position.

Optionally, determining a three-dimensional measurement between the first point and the second point in the area based on the determined size of the area and the generated three-dimensional model of the area comprises determining the point-to-point distance between the first position and the second position.

Optionally, the method further comprises: defining a plane in the area based on the identified first and second points; and determining a three-dimensional area based on the defined plane.

Optionally, the method is performed on a computing device located in a surgical theater.

Optionally, the method is performed on a cloud-based computing device.

Optionally, the object is a pointing tool.

Optionally, the object is a drill guide.

Optionally, the object is a shaver.

Optionally, the object is a radio frequency (RF) probe.

Optionally, the object is an arthroscopic tool with a rigid component.

Optionally, the first point on the one or more two-dimensional images and the second-point on the one or more two dimensional images are located on a contour of an internal area patient to be grafted, and wherein the method comprises: transmitting the captured one or more two-dimensional images of the internal area from the received data to a projector, wherein the projector is configured to project the captured one or more two-dimensional images onto a graft positioned in a field of view of the projector; and transmitting the determined three-dimensional measurement between the first point and the second point in the area to the projector, wherein the projector is configured to scale the projected one or more two-dimensional images onto the graft positioned in the field of view of the projector based on the determined the determined three-dimensional measurement between the first point and the second point in the area.

Optionally, an internal area of the patient to be grafted comprises a section of cartilage of the patient.

Optionally, an internal area of the patient to be grafted comprises a vessel of the patient.

Optionally, an internal area of the patient to be grafted comprises a ligament of the patient.

Optionally, the first point on the one or more two-dimensional images is located on an end of a tool, the second-point on the one or more two dimensional images are located on an anatomical feature of the patient, and wherein the method comprises: comparing the determined three-dimensional measurement between the first point and the second point in the area to a pre-determined threshold; and transmitting a notification to a user if the determined three-dimensional measurement between the first point and the second point in the area is less than the pre-determined threshold Optionally, identifying the second point on the one or more two dimensional images comprises: identifying a fluoresced anatomical feature in the one or more captured two-dimensional images; and determining the contours of the fluoresced anatomical features using the generated three-dimensional model.

Optionally, identifying the second point on the one or more two dimensional images comprises: applying a machine learning classifier to the one or more captured two-dimensional images to determine the location of an anatomical feature within the one or more captured two-dimensional images, wherein the machine learning classifier is trained using a plurality of training images that comprise the anatomical feature fluoresced within the training image; and determining the contours of the anatomical feature using the generated three dimensional model.

Optionally, the anatomical features includes a nerve and/or blood vessel of the patient.

Optionally, determining a size of the three-dimensional area of the three-dimensional model based on the one or more fiducial markers of the object comprises applying one or more machine learning models to the captured one or more two-dimensional, wherein the one or more machine learning classifiers are configured to estimate a pose of the object.

Optionally, the estimated pose of the object generated by the one or more machine learning models are used to determine a ratio between an actual size of the object, and a size of the object in the image, and wherein determining the size of the three-dimensional area of the three-dimensional model is based on the determined ratio.

Optionally, identifying a first point on the one or more two-dimensional images comprises identifying a point on a first surgical tool visualized in the one or more two-dimensional images, wherein identifying a second point on the one or more two-dimensional images comprises identifying a point on a second surgical tool visualized in the one or more two-dimensional images, and wherein determining a three-dimensional measurement between the first point and the second point in the area based on the determined size of the three-dimensional area and the generated three-dimensional model of the area comprises determining a three-dimensional measurement between the identified point on the first surgical tool and the identified point on the second surgical tool.

Optionally, the one or more fiducial markers of the object comprise one or more ArUco markers configured to identify information pertaining to the size of the object.

Optionally, the one or more ArUco markers comprise one or more bit patterns encoded with error correction.

Optionally, the one or more ArUco markers are square shaped.

Optionally, determining a size of a three-dimensional area of the three-dimensional model based on the one or more fiducial markers of the object configured to indicate the pre-determined dimension comprises: locating the one or more ArUco markers in the captured one or more two-dimensional images; and identifying the ArUco markers in the captured one or more two-dimensional images.

Optionally, identifying the ArUco markers in the captured one or more two-dimensional images comprises applying one or more computer vision processes to the captured one or more two-dimensional images.

Optionally, the one or more computer vision processes are calibrated using a calibration device, wherein the calibration devices comprises: a chamber, wherein the chamber is configured to be filled with a liquid; one or more test ArUco markers, wherein the test ArUco markers are disposed within the chamber; and an imaging device interface, wherein the imaging device interface is configured to receive an imaging device, and position the imaging device so that the imaging device can view the one or more test ArUco markers disposed within the chamber.

Optionally, calibrating the one or more computer vision processes comprises: generating one or more images of the one or more test ArUco markers within the chamber of the calibration device using an imaging device connected to the imaging device interface of the calibration device; and applying a correction factor to the one or more computer vision processes, wherein the correction factor is based on the generated one or more images.

Optionally, the one or more annotated images to train the machine learning model comprises synthetic training images.

In one or more examples, a method for tracking a location of a fixed point in endoscopic images comprises: receiving video data captured from an endoscopic imaging device configured to image an internal area of a patient; capturing a first two-dimensional image of the internal area from the received video data; receiving a selection from a user of a location on the first two-dimensional image on which to place a graphical marker; placing a graphical marker at a location on the first two-dimensional image; detecting a first location of an interest point in the first two-dimensional image, wherein detecting the location of an interest point comprises applying a machine learning model to the first two-dimensional image to identify the interest point; capturing a second two-dimensional image of the internal area from the received video data; detecting a second location of the interest point from the first two-dimensional image in the second two-dimensional image, wherein detecting the interest point comprises applying a machine learning model to the second two-dimensional image to identify the interest point; determining a distance and direction between the first location and the second location; and placing the graphical marker on the second two-dimensional image based on the determined distance and direction between the first location and the second location.

Optionally, the determining the distance and direction between the first location and the second location comprises applying a k-nearest neighbors (KNN) algorithm to both the first and second two-dimensional images.

Optionally, determining distance and direction between the first location and the second location comprises applying homography to the first and second two-dimensional images.

Optionally, the method comprises: if the determined distance and direction between the first location and the second location is such that the graphical marker cannot be placed on the second image, then placing a graphical indicator on the second image configured to point to the direction in which the graphical marker would be located.

In one or more examples, a method for generating a three-dimensional model of an internal area of a patient using endoscopic images comprises: receiving video data captured from an endoscopic imaging device configured to image an internal area of the patient; capturing a plurality of two-dimensional images of the internal area from the received video data, detecting a first location of an interest point in a first two-dimensional image of the plurality of two-dimensional images; detecting a second location of the interest point in a second two-dimensional image of the plurality of two-dimensional images; determining a motion vector between the first two-dimensional image and the second two-dimensional image; combining the first two-dimensional image and the second two-dimensional image to form a third two-dimensional image, wherein the combining is based on the determined motion vector between the first two-dimensional image and the second two-dimensional image; acquiring depth information from the first two-dimensional image and the second two-dimensional image; and generating a three-dimensional model of the internal area based on the third two-dimensional image and the acquired depth information.

Optionally, generating a three-dimensional model of the internal area based on the third two-dimensional image and the acquired depth image comprises applying a structure from motion procedure to the first and second two-dimensional images to generate the three-dimensional model of the internal area.

Optionally, determining the motion vector between the first two-dimensional image and the second two-dimensional image comprises applying homography to the first and second two-dimensional images.

Optionally, the method comprises generating a graphical overlay of a drill trajectory onto a two-dimensional image of the plurality of two-dimensional images using the generated three-dimensional model of the internal area.

Optionally, generating the graphical overlay comprises associating the generated three-dimensional model with an external model of the internal area.

Optionally, the external model is a computerized tomography (CT) scan of the internal area.

Optionally, the external model is a SOMA database tailored anatomical scan representing the internal area.

Optionally, the external model is a modified version of the generated three-dimensional model.

Optionally, the graphical overlay comprises a representation of the optimal drill trajectory for a given surgical procedure involving the internal area.

Optionally, the graphical overlay comprises a representation of an estimated result of a current drill trajectory.

Optionally, the graphical overlay comprises a representation of a portion of the internal area where drilling is to be avoided.

In one or more examples, a method for generating an augmented reality overlay on a two-dimensional image of an internal area of a patient comprises: receiving a three-dimensional model of the internal area; registering a two-dimensional image of the internal area with the received three-dimensional model of the internal area; and overlaying a three-dimensional graphical overlay on the two-dimensional image based on the registration between the two-dimensional image of the internal area and the received three-dimensional model of the internal area.

Optionally, the method comprises adjusting a position of the three-dimensional overlay based on a motion of the two-dimensional image of the internal area.

Optionally, the motion of the two-dimensional image is determined using a process comprising: capturing a plurality of two-dimensional images of the internal area from the received video data, detecting a first location of an interest point in a first two-dimensional image of the plurality of two-dimensional images; detecting a second location of the interest point a second two-dimensional image of the plurality of two-dimensional images; and determining a motion vector between the first two-dimensional image and the second two-dimensional image.

Optionally, determining the motion vector between the first two-dimensional image and the second two-dimensional image comprises applying homography to the first and second two-dimensional images.

Optionally, the motion of the two-dimensional image is determined using EM tracking.

Optionally, registering a two-dimensional image of the internal area with the received three-dimensional model of the internal area is performed at a pre-defined time interval.

BRIEF DESCRIPTION OF THE FIGURES

The invention will now be described, by way of example only, with reference to the accompanying drawings, in which.

DETAILED DESCRIPTION

Figure 1:
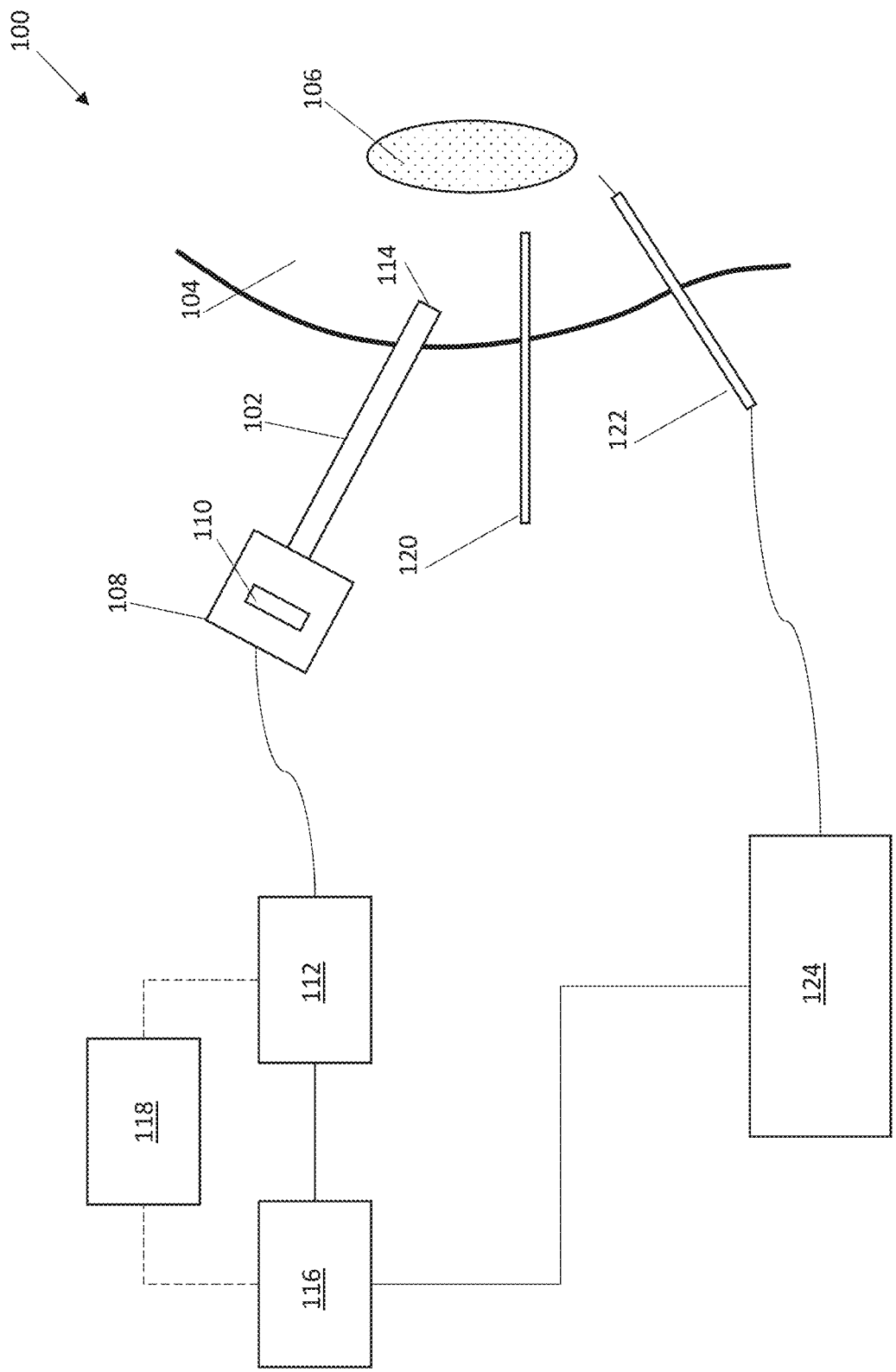
FIG. 1 illustrates an exemplary endoscopy system according to examples of the disclosure.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are systems and methods for measuring three-dimensional distances using endoscopic images, such as in an internal area of a patient, e.g. during a minimally invasive surgical procedure. According to various embodiments, one or more images are captured from a video feed recorded from an endoscope during a surgical procedure. The video feed may be pre-recorded, i.e. recorded prior to measuring the three-dimensional distances. Alternatively, the video feed may be real-time. The video feed may be recorded from an endoscope that is pre-inserted in an internal area of the patient, i.e. inserted in the internal area of the patient prior to measuring the three-dimensional distances. The captured images include images of a fiducial marker that, as described further below, can be used as a reference to determine the actual size of the image. The fiducial marker can be used to determine the actual distance between two points in an image based on the measured distance between two points on the image. Using the images, a three-dimensional model of the surgical space can be generated. The three-dimensional model can be generated by applying a structure-from-motion algorithm to the images to generate a three-dimensional model that also includes depth information about the surgical space pictured in the endoscopic images. Additionally or alternatively, the three-dimensional model can be generated by using the images as well as a time of flight sensor located in the surgical space or on the camera itself.

The three-dimensional model of the surgical space can allow the user, e.g. the surgeon, to accurately measure distances between two points (or determine other geometrical measurements such as area). With respect to distances between two points on an image, a user can provide the system with an indication of when to begin a measurement using a pointing tool. The user can then move the tool the desired length and then provide an indication to the system of where the end point of the measurement is. Based on the indicated beginning and end point of the measurement, and using the three-dimensional model, the system can determine the three-dimensional distance between the two points.

In one or more examples, when the user indicates the beginning point of a measurement to be taken, the systems and methods described herein can use one or more machine learning models, such as an object detector, to determine the distal end of the pointing tool, so as to determine the exact point in the image from which to begin the measurement. When the user moves the pointing tool and indicates the end of the measurement, the systems and methods described herein can also use the one or more machine learning models to determine the precise end point of the measurement to be taken, and can then use the three-dimensional model and the size information from the fiducial marker to generate an accurate measurement of the distance between the beginning point and end point.

The machine learning models can be generated using a supervised training process. The supervised training process can include the use of training images that are annotated with the known characteristics of the image. These training images (i.e., images that contain known characteristics and are identified as such through the annotations) can be then processed by the machine classifiers so as to configure each of the machine classifiers. In one or more examples, the machine learning models can be generated using other training processes including semi-supervised and unsupervised processes. For instance, in one or more examples the machine learning models can be generated using such approaches as Bootstrap Your Own Latent (BYOL) self-supervised learning, SimCLR self-supervised learning, Simple Siamese Representation Learning ("SimSiam") unsupervised learning, and Swapping Assignments between Views ("SwAV") unsupervised learning techniques. The machine learning models can include an instrument type classifier that is configured to identify the type of tool pictured in a surgical space. According to various embodiments, the machine learning models are implemented using one or more convolutional neural networks (CNN). Additionally or alternatively, in one or more examples, the machine learning models can be implemented using a Self-Supervised Transformed with Energy-based Graph Optimization (STEGO) process. Other examples of machine learning models that can be employed in the systems and methods described herein can include Greedily Learned Accurate Matching (GLAM), DeepLabV3, Wide-ResNet, and DPT. In one or more examples, the example model architectures provided above are meant as examples only and should not be seen as limiting in any way. In one or more examples, any machine learning models discussed herein could be implemented using other known machine learning models not listed herein.

Once the tool pictured in the image is identified using the one or more machine learning models, the tool can be segmented from the image, and the location of the distal end of the tool can be determined based on the segmented portion of the image or images.

By generating a three-dimensional model of the surgical space and by precisely determining the location of the beginning point and end point of the measurement to be taken, the systems and methods described herein can provide a more precise and accurate measurement of the distances between two points (or other geometric measurements) versus the conventional practice of a surgeon estimating the distance by looking at the video data provided by an endoscopic imaging device.

In the following description of the various embodiments, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present disclosure as described herein.

FIG. 1 illustrates an exemplary endoscopy system according to examples of the disclosure. System 100 includes an endoscope 102 for insertion into a surgical cavity 104 for imaging tissue 106 within the surgical cavity 104, e.g. during a medical procedure. The endoscope 102 may extend from an endoscopic camera head 108 that includes one or more imaging sensors 110. Light reflected and/or emitted (such as fluorescence light emitted by fluorescing targets that are excited by fluorescence excitation illumination light) from the tissue 106 is received by the distal end 114 of the endoscope 102. The light is propagated by the endoscope 102, such as via one or more optical components (for example, one or more lenses, prisms, light pipes, or other optical components), to the camera head 108, where it is directed onto the one or more imaging sensors 110. One or more filters (not shown) may be included in the endoscope 102 and/or camera head 108 for filtering a portion of the light received from the tissue 106 (such as fluorescence excitation light).

The one or more imaging sensors 110 generate pixel data that can be transmitted to a camera control unit 112 that is communicatively connected to the camera head 108. The camera control unit 112 generates a video feed from the pixel data that shows the tissue being viewed by the camera at any given moment in time. In one or more examples, the video feed can be transmitted to an image processing unit 116 for further image processing, storage, display, and/or routing to an external device (not shown). The images can be transmitted to one or more displays 118, from the camera control unit 112 and/or the image processing unit 116, for visualization by medical personnel, such as by a surgeon for visualizing the surgical field 104 during a surgical procedure on a patient.

As will be described further below, the system 100 can include a fiducial marker 120 that can be inserted into the surgical cavity 104 by a surgeon. The fiducial marker can include information about the size of the maker 120 for instance by including one or more markings indicating a known size or distance, or information about the size of the tool or a portion thereof (that can be accessed using a barcode located on the fiducial marker). As will be described in further detail below, the fiducial marker 120 can be used to scale the images collected by the endoscope 102, so that the system can determine the actual distances between two points in the image based on the location of the points as they appear in the image.

In one or more examples, the system 100 can include a pointing tool 122 connected to a tool controller 124. The tool controller 124 can be configured to control and/or operate the pointing tool 122. The user, e.g. the surgeon, can place the pointing tool at a particular location in the surgical cavity 104 and press a button on the tool to indicate where to begin taking a measurement. The controller 124 can recognize the indication from the user and communicate that indication to the image processing unit 116. The image processing unit 116 can then determine the precise location within an image from which to begin taking a measurement. The user can also press a button on the tool to indicate where the end point of a measurement is. The controller 124 can recognize the indication from the user and communicate the indication to the image processing unit 116. The image processing unit 116 can use the information provided from the controller 125 to determine the precise location within the image of the end point of the measurement.

In one or more examples, and as described further below, the image processing unit 116 can use the information regarding the beginning and end point of the measurement to determine the exact pixels within an image to set the beginning point and end point of the measurement. The image processing unit 116 can use one or more machine classifiers to segment the pointing tool from the image and determine the location of the distal end of the pointing tool 122 at the precise moments when the surgeon indicated both the beginning point and end point of the measurement to be taken.

Using the three-dimensional model, the size information from the fiducial marker, and the location of the beginning point and end point of the measurement, the system 100 can determine the three-dimensional distance between the beginning point and end point. By generating a three-dimensional model, and by precisely locating the beginning point and end point of the measurement, the system 100 can accurately determine the measurement with a higher degree of precision than if a surgeon estimated the measurement using the endoscopic images themselves. Furthermore, the system 100 is able to determine precise three-dimensional measurements using two-dimensional endoscopic image data.

Using two-dimensional images alone to determine distances between two points (as is conventionally done) can lead to inaccurate measurements. Two-dimensional images by themselves can obscure depth information and only show changes in position in two dimensions. Thus, while a two-dimensional image may be able to accurately illustrate the changes in both the x-axis and y-axis, they may not accurately depict changes in the z-axis (i.e., depth). Thus, using two-dimensional images alone to measure distance may not produce accurate results. An example scenario in which measuring a distance between two points using a two-dimensional image leads to inaccurate results is provided below.

Figure 2A:
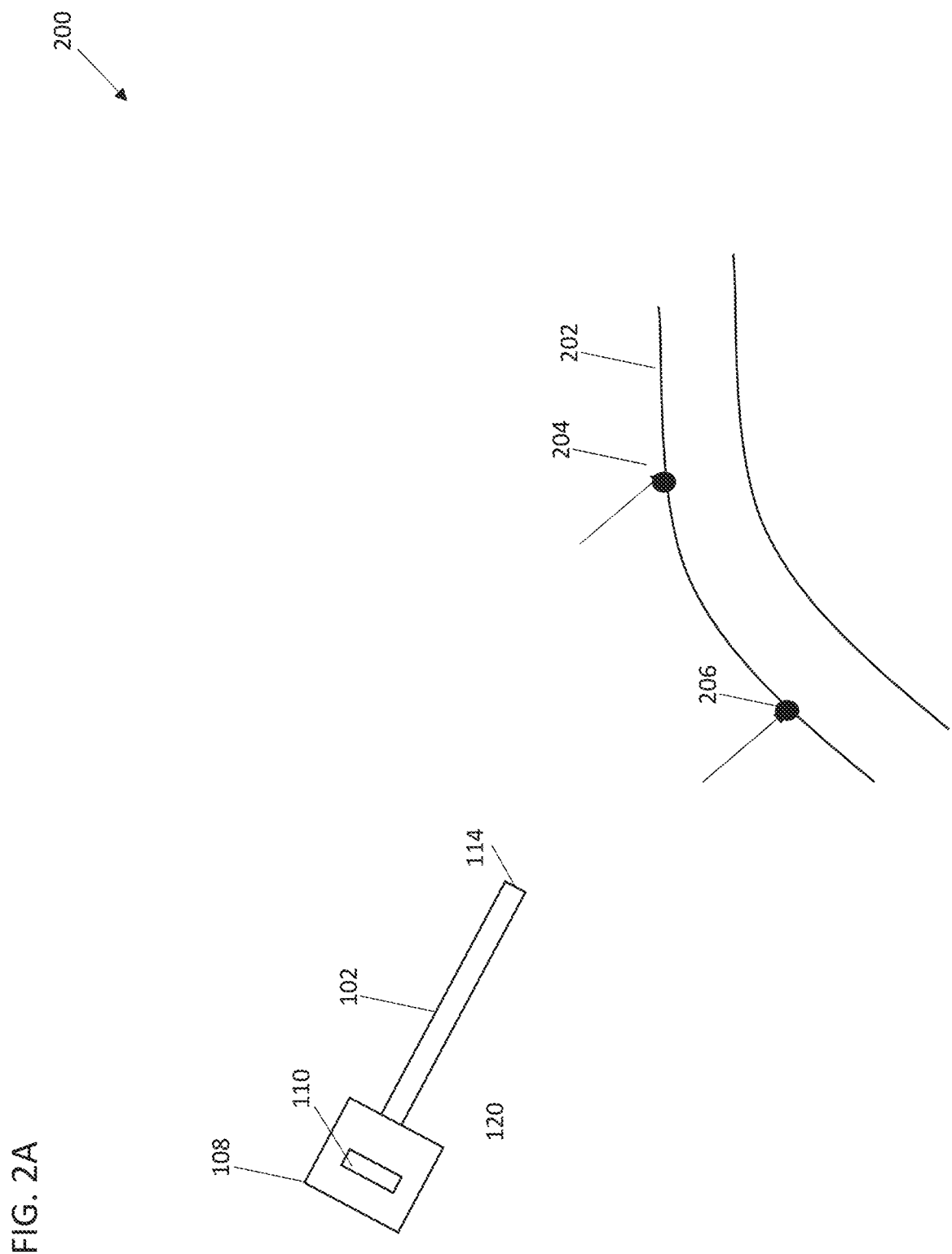
FIG. 2A illustrates an exemplary three-dimensional measurement according to examples of the disclosure.

FIG. 2A illustrates an exemplary three-dimensional measurement according to examples of the disclosure. In the example 200 of FIG. 2A, an endoscope 102 extending from an endoscopic camera head 108 that includes one or more imaging sensors 110 can be used to visualize a surface 202 within a surgical cavity. The surface 202 can represent a particular anatomic feature within the human body. In the example 200 of FIG. 2, the surface 202 can be curved in a manner (described in further detail below) that may be obscured in a two-dimensional representation of the surface 202 based on a two-dimensional image captured by the endoscope 102.

A user may wish to take a measurement between two points along the surface 202. For instance, the user may wish to measure the distance between the point 204 and 206 as illustrated in FIG. 2. Any measurement between two points on the surface 202 should take into account the curvature of the surface 202, however because the endoscope 102 is viewing surface 202 from above, the curvature of surface 202 (which from the perspective of the endoscope 102 would appear as a change in depth) may be obscured in a two-dimensional image taken from endoscope 102.

Figure 2B:
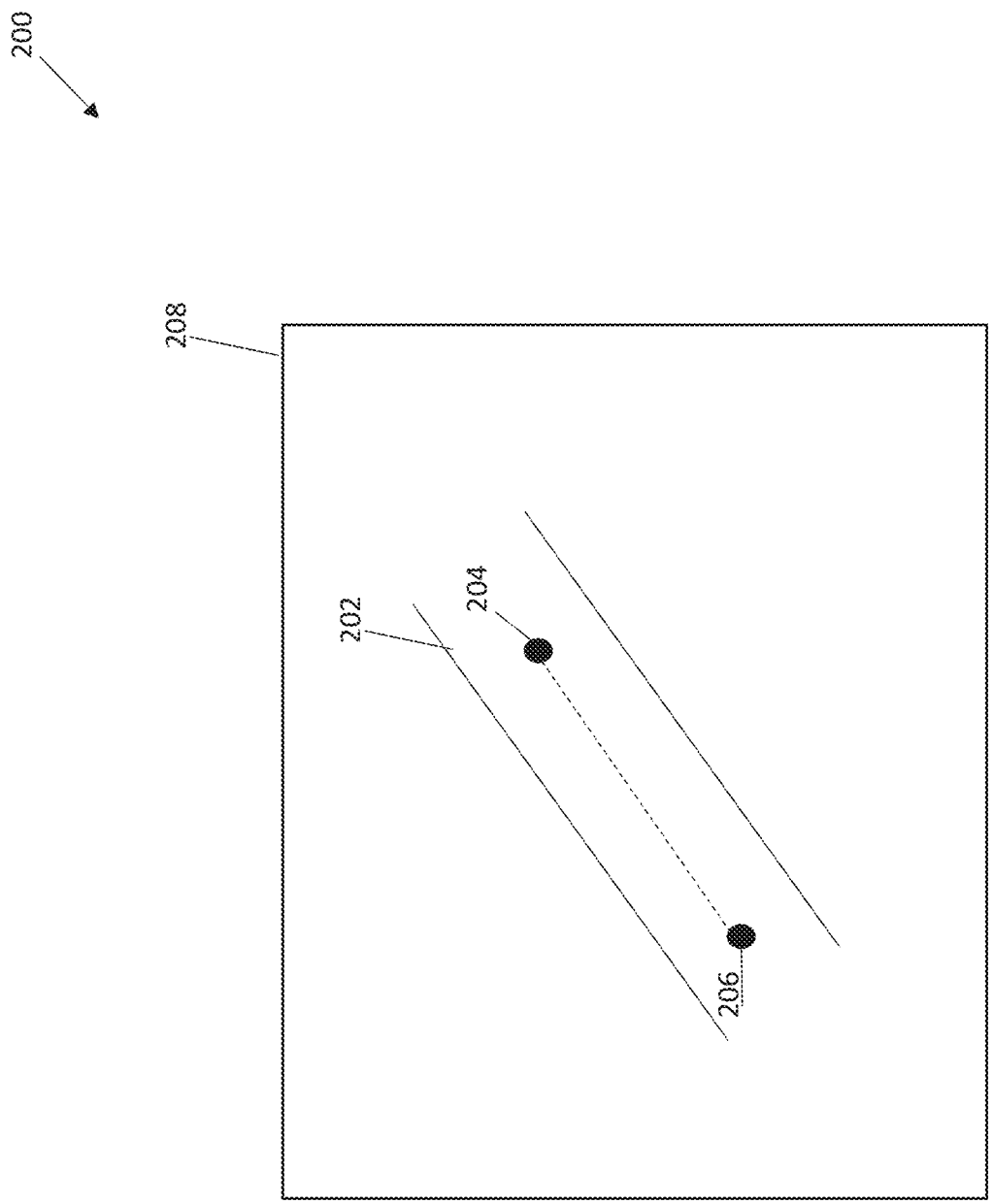
FIG. 2B illustrates an exemplary measurement taken from a two-dimensional image according to examples of the disclosure.

FIG. 2B illustrates an exemplary two-dimensional image taken from an endoscope of a three-dimensional surface according to examples of the disclosure. FIG. 2B represents a two-dimensional image of the surface 202 taken by an endoscope pointed above the surface 202 as shown in FIG. 2A. As shown in the image 208, due to the camera's position, the surface 202 (which is actually curved) appears flat. This is due to the position of the endoscope relative to surface 202, as well as the fact that the image is two-dimensional and thus will obscure any features in the third dimension (i.e., depth). Due to the endoscope's position relative to the surface 202, the curvature of the surface 202 will appear as variations in the depth of the image which may not be represented in the two-dimensional image 208 taken by endoscope 102. If a surgeon, using image 208, wanted to measure the distance between points 204 and 208 he can estimate the distance using the displacement between the two points in the x and y directions, but may not be able to accurately account for variations in depth because the image 208 does not depict the changes of depth in the image. Thus, the surgeon either has to account for the changes in depth somehow (through their own estimation) or use a measurement that does not account for the depth and thus does not represent the true distance between the points 204 and 206.

Because an endoscope produces two-dimensional image data, in one or more examples of the disclosure, in order to use the images to measure distances, information regarding depth can be captured from the images in order to build a three-dimensional model that can account for changes in depth in an image. The depth information can be derived from the images using image processing techniques described below, or can be collected using specialized equipment that can record depth information and correlate the depth information to the images acquired by the endoscope.

Figure 3:
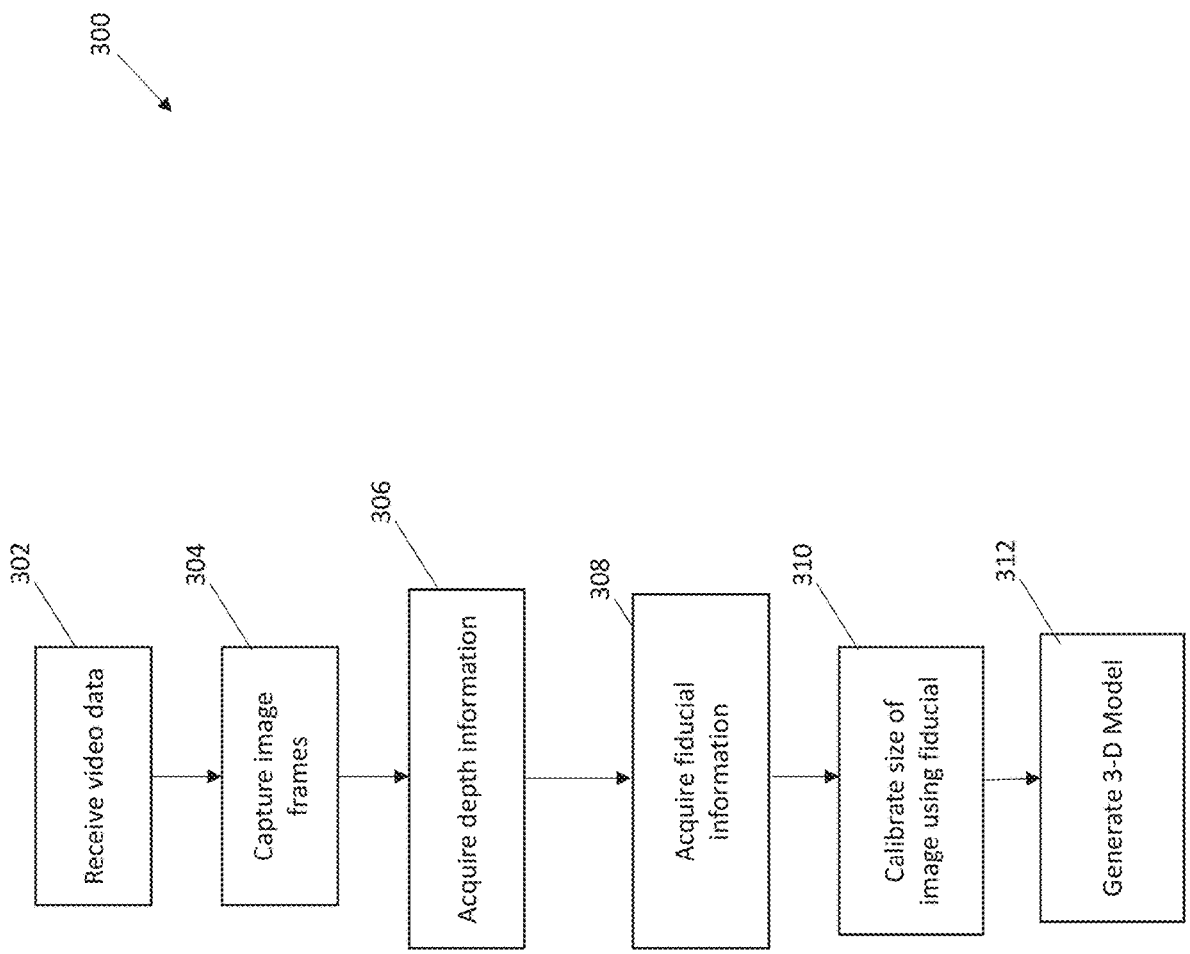
FIG. 3 illustrates an exemplary method for generating a three-dimensional model of a surgical field using two-dimensional images according to examples of the disclosure.

FIG. 3 illustrates an exemplary method for generating a three-dimensional model of a surgical field using two-dimensional images according to examples of the disclosure. In one or more examples of the disclosure, the process 300 of FIG. 3 can begin at step 302 wherein video data is received from the endoscopic imaging device. The endoscope may be pre-inserted prior to start of the process 300. The video data received from the endoscopic imaging device can be displayed on a screen so that the surgeon can view in real-time the video data received from the endoscopic device.

Once the video data is received at step 302, the process 300 can move to step 304 wherein one or more image frames are captured from the video data. The video data received at 302 can be continuous showing a real-time view of what the endoscopic imaging device is seeing. In one or more examples, "capturing" image frames at step 304 can include capturing one or more two-dimensional still images from the video data (i.e., generating and storing a screen shot of the video data). The images can be captured at step 304 based on an indication or signal provided by the user to capture the one or more images. For instance, in one or more examples, the user can push a button on a tool or on the endoscopic device itself to capture a first image and can keep pushing the button on the tool to capture subsequent images from the video data received at step 302 from the endoscopic imaging device. In one or more examples, as the video data from the endoscope is playing in real-time, the user can push a button, and the frame of the video associated with the time that the user pushed the button can be captured. The user can direct the capture of an image at step 304 by providing input to a graphical user interface provided on the screen on which the video data from the endoscopic imaging device is displayed. Additionally or alternatively to the examples described above, the user can direct the device to capture an image by pushing a foot pedal located by their foot. As will be described in the further detail below, the user can capture images in a manner that allows for three-dimensional depth information to be extracted from the two-dimensional images captured at step 304. As will be further described below, the user can direct the capture of images so as to use those images to acquire depth information about the surgical space visualized in the images.

Once the images have been captured at step 304, the process 300 can move to step 306 wherein depth information regarding the surgical space can be acquired. As described above, the images of the surgical space provided by the endoscopic imaging device themselves may not be able to provide depth information, since the images are in two dimensions and thus may obscure variations in a third dimension (i.e., depth). In one or more examples, at step 306, the depth information can be acquired using a time-of-flight sensor that is inserted in the surgical cavity that is being visualized by the endoscopic imaging device. In one or more examples of the disclosure, a time-of-flight sensor can be configured to measure the time it takes for a signal to travel from the sensor, bounce off a surface within the surgical cavity, and return back to the sensor. The time it takes to measure this "time of flight" can be proportional to the depth of the surface. Thus, the longer the time of flight, the deeper the surface is at a given point. Thus, in one or more examples, a time-of-flight sensor can be used to map the depth of the entire surgical cavity visualized by the endoscopic device. In one or more examples the entire surgical space can be mapped using a time-of-flight sensor to acquire depth information, and the depth information can be correlated to the images captured at step 304.

In one or more examples, at step 306, the depth information can be acquired from the images captured at step 304. For instance, and as described in further detail below, the depth information at step 306 can be acquired using a structure-from-motion algorithm that can be applied to the images captured by the user. Structure-from-motion can refer to a technique for estimating three-dimensional structures from two-dimensional image sequences. In one or more examples, the user can direct the capture of images from the endoscopic data such that the images can be used by the structure-from-motion algorithm to acquire depth information about the surgical space. Alternatively, or in addition to the examples above, a single image can be used to acquire depth information using a machine learning model that takes a single image as an input and approximates depth from that image.

In one or more examples, at step 306, depth information can be acquired using a stereo camera that is part of the endoscopic imaging device or is situated on a separate device. A stereo camera can refer to a camera with multiple lenses focusing onto separate sensors (i.e., image sensors) that combine to provide stereo views of images thus giving the device the ability to capture three-dimensional images. Data provided by a stereo camera can be used to generate depth information about the surgical space. As described, a number of techniques, either alone or in combination, can be used to acquire depth information. These techniques and devices can be used to augment the image data captured at step 304 so as to provide information about variations in depth that may be obscured by the two-dimensional images captured at step 304.

Once the depth information is acquired at step 306, the process 300 can move to step 308 wherein information about a fiducial present in the surgical cavity can be acquired. A "fiducial" can refer to an object that can be used as a point of measure. In other words, a fiducial can be an object that is placed in the surgical cavity that has a known size and/or represents a known size that can be used as a basis of comparison to understand the size of other objects. Features shown in an image can vary in size based upon the zoom level, or focal length, of the camera used to acquire the image, or upon the proximity of the camera to the anatomy of the image (e.g. the working distance). For instance, if the camera is zoomed into the surgical cavity, or is positioned closer to the surgical cavity, then features in the surgical cavity can appear larger than if the camera was zoomed out or was positioned further away. Thus, in one or more examples, a fiducial or fiducial marker can be inserted into the surgical space and be visualized by the endoscopic imaging device so as to provide a known size reference that can be used to calibrate the sizes of other objects or features that appear in the image. The fiducial can provide the calibration measurements that can be used to determine the size of other objects pictured in the surgical space. As will be described later below, the fiducial marker can be used to calibrate the measurements taken in the surgical space.

In one or more examples, the fiducial marker can be implemented by markings on a tool or object inserted into the surgical cavity that are a known distance apart from each other. For instance, a fiducial marker can be implemented by using two laser etched markings on a tool that are at a predetermined distance, e.g. 2 mm apart, from one another. In the image that includes the fiducial, the markings may appear to be greater or less apart depending on the zoom level or working distance of the imaging device used to capture the image. However, since it is known that the markings are exactly 2 mm apart, the distance that those markings appear to be apart from each other in the image can be used to determine the size of all the other objects in the image (including measurements taken by a surgeon as discussed in further detail below).

Figure 4:
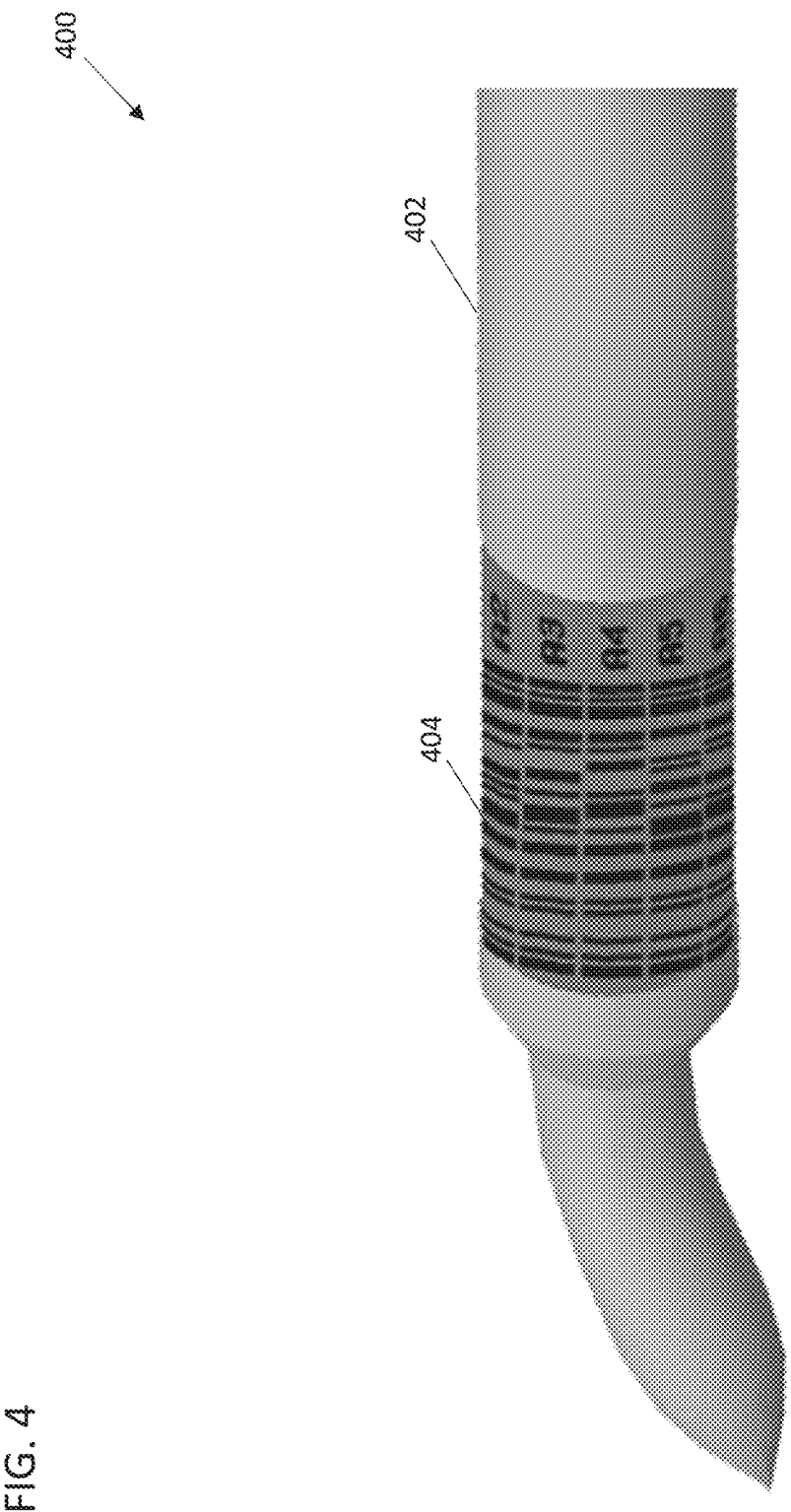
FIG. 4 illustrates an exemplary fiducial marker according to examples of the disclosure.

In one or more examples, rather than markings, the fiducial can take the form of a set of barcodes that can be read from the image of the fiducial. The barcode can be of a known size, and/or the system can use the barcode to access size information about the tool that has the barcode. FIG. 4 illustrates an exemplary fiducial marker according to examples of the disclosure. In the example of FIG. 4, the tool 402 that is inserted into the surgical cavity and visualized by the endoscopic imaging device can include one or more barcodes 404. The tool 402 can include multiple barcodes that are e.g. positioned around the device, so that the orientation of the device can be ascertained using the barcodes that are visible in the image from the endoscopic imaging device. By knowing the orientation of the tool, the fiducial information provided by the tool can provide more accurate calibration. In one or more examples, instead of a barcode, the fiducial marker can instead include a Quick Response (QR) code. Alternatively or additionally, the fiducial marker can include one or more ArUco markers that include one or more bit patterns that are square shaped and may include one or more bit patterns encoded with error correction. ArUco markers can be especially suited to fiducial marker identification because they include large "bits" designed to be easily recognizable under a range of conditions. Furthermore, they include bit patterns that can be encoded with error correction that can lead to more robust detection with fewer false positives. The square shape of the ArUco marker can allow for an easy visual indicator of skew and thus simplifies the process of determining the orientation of the tool, and the detection yields an identification number and pixel coordinate locations of all four corners. In one or more examples, a pointer can have a ArUco marker placed on a hexagon, pentagon, or rectangle section of the pointer to ensure that the markers on the ArUco marker lay on a flat plane. Additionally or alternatively to Aruco markers, the fiducial markers can include one or more AprilTags, which can be used to identify a fiducial marker in the image. Throughout the disclosure, it should be understood that references to a barcode can also be alternately implemented as a QR code, ArUco marker and/or AprilTag. In one or more examples, a pose estimation machine learning model can be applied to the images to estimate a pose of the tool in the image. In one or more examples, the pose (i.e., the orientation of the tool in the image) combined with fiducial marker data can be used to determine a ratio between an actual size of the tool, and the size of the object in the image, so as to provide overall fiducial information to the process 300.

Returning to the example of FIG. 3, once the fiducial information is acquired at step 308, the process 300 can move to step 310 wherein the size of the image is calibrated using the fiducial information acquired at step 308. As discussed above, calibrating the size of the image can include using the fiducial to determine the size of other features present in the images acquired at step 304, and to calibrate the size of the image overall so that the distances between pixels in the image can be correlated to real-life distances based on how large or small the fiducial appears in the image. As will be discussed in further detail below, the calibration performed at step 310 of process 300 can be used to not only generate a three-dimensional model of the surgical cavity visualized by an endoscopic imaging device, but can also be used to allow the surgeon to take accurate three-dimensional measurements in the surgical space during a minimally invasive surgical procedure.

Once the size of the image has been calibrated using the fiducial at step 310, the process 300 can move to step 312, wherein a three-dimensional model of the surgical cavity is visualized by the endoscopic imaging device. A three-dimensional model of the surgical space can be configured to show variations in the x, y, and z directions of the surgical cavity. The images taken from the endoscopic imaging device can themselves provide information about variations in the x and y directions since the images are two-dimensional, and the depth information acquired using techniques and devices described above can provide the information about variations in the z direction. The fiducial information can provide scale information about variations observed in the two-dimensional images as well as the depth information. As will be described in further detail below, the three-dimensional model can be used to generate accurate measurements of lengths or other geometric features during a minimally invasive surgical procedure.

Figure 5:
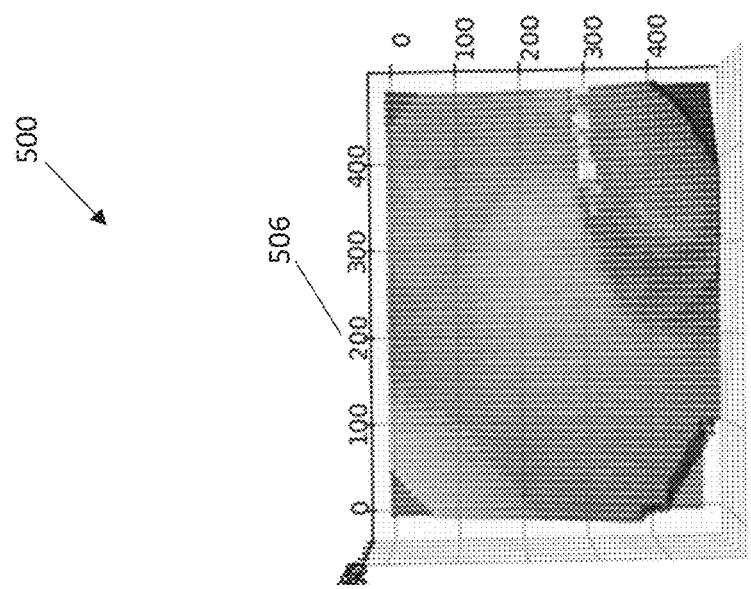
FIG. 5 illustrates an exemplary three-dimensional model of a surgical field according to examples of the disclosure.
Figure 5:
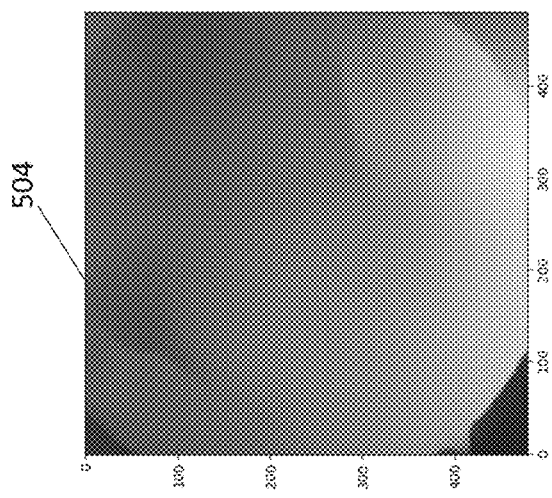
Figure 5:
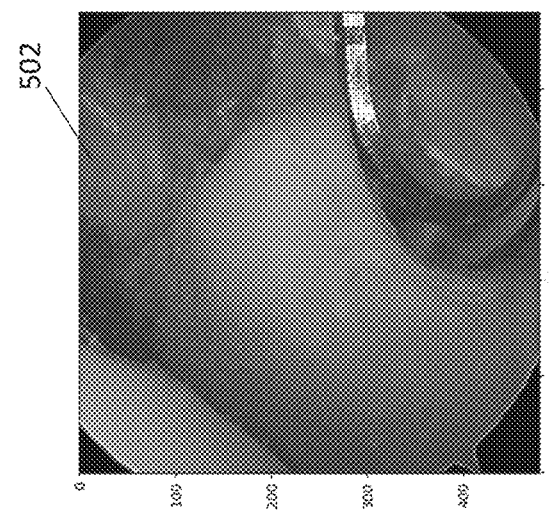

FIG. 5 illustrates an exemplary three-dimensional model of a surgical field according to examples of the disclosure. In the example 500 of FIG. 5, image 502 can represent a two-dimensional image acquired at step 304 of FIG. 3. As shown in image 502, variations in the x and y direction can be shown in the image because the two dimensions are represented in the image. However, because the image 502 is two-dimensional, image 502 may obscure variations in the z direction (i.e., depth). Image 504 represents a visual depiction of depth information according to examples of the disclosure. In the example of image 504, depth can be represented by the darkness of the shading, with darker shaded areas representing larger depths, and lightly shaded areas representing shallower depths. Image 504 is merely provided as an example way of representing depth information and should not be seen as limiting. It can be appreciated that depth information can be stored in numerous ways including as numerical data. Image 504 can be generated by the depth information acquired at step 306 of the process 300 depicted in FIG. 3. As described above, the depth information can be correlated to the image 502 by indicating the position on the image corresponding to a particular depth value. Thus, each depth value can be correlated to a specific pixel in the image 502.

Image 506 illustrates an exemplary three-dimensional model according to examples of the disclosure. The three-dimensional model can include a three-dimensional axis that maps variations in the x, y, and z directions across an image to form a three-dimensional image of the surgical cavity visualized by the endoscopic imaging device. The three-dimensional model can also use the size calibration information provided by the fiducial as described in step 308 and 310 of the process 300 depicted in FIG. 3. In one or more examples, the size information can be used to scale the three-dimensional model to size so that variations depicted in the three-dimensional model 506 are scaled to the actual size of the variation.

Figure 6:
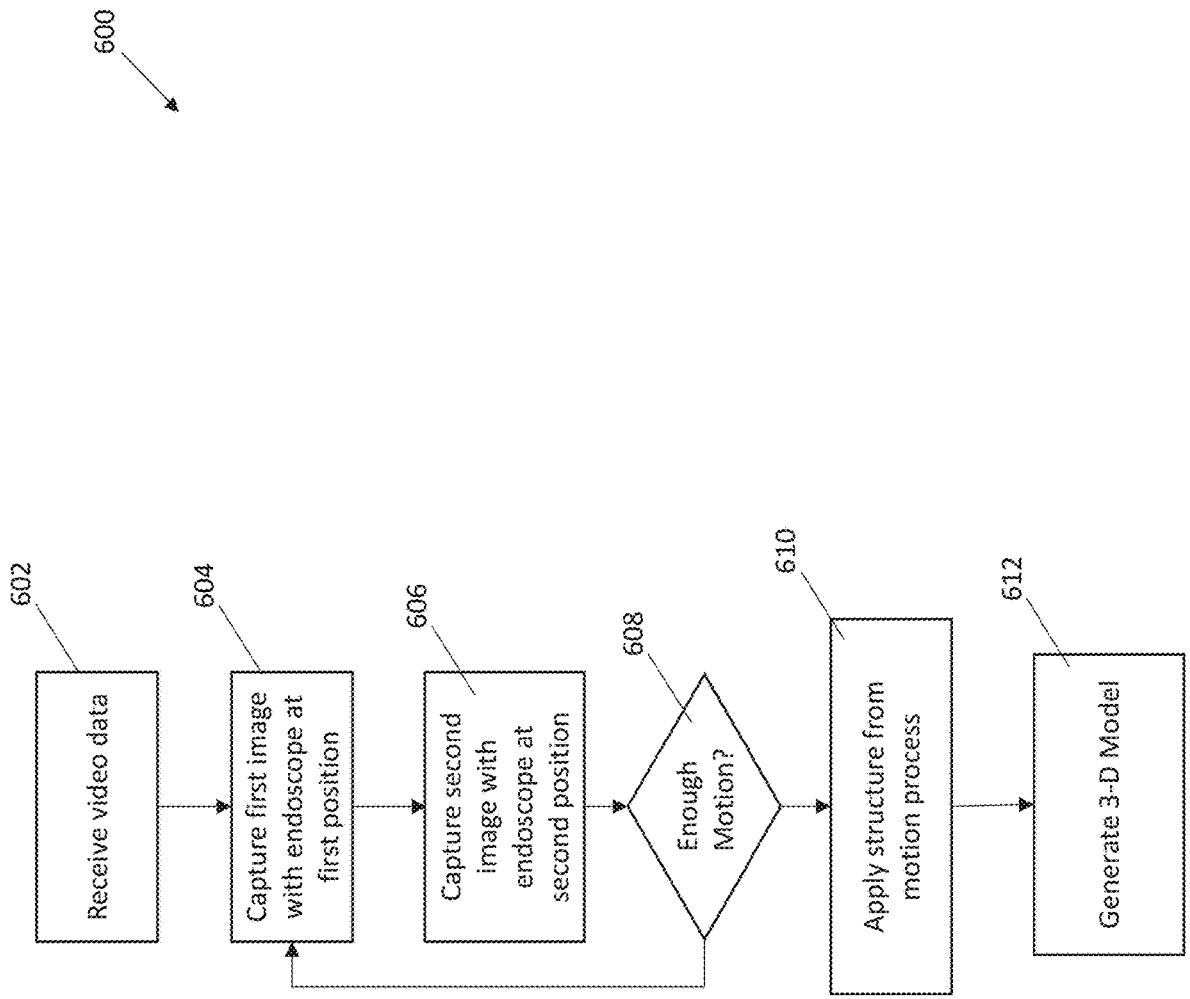
FIG. 6 illustrates an exemplary method for acquiring depth information from one or more two-dimensional images taken from an endoscopic imaging device according to examples of the disclosure.

Returning to the example of FIG. 3, and as described above, acquiring depth information at step 306 can include applying a structure-from-motion algorithm to images acquired at step 304 of process 300. FIG. 6 illustrates an exemplary method for acquiring depth information from one or more two-dimensional images taken from an endoscopic imaging device according to examples of the disclosure. The process 600 illustrated in FIG. 6 can begin at step 602 wherein video data is received from the endoscope in the same manner as described above with respect to step 302 of process 300 in FIG. 3. The endoscope can be pre-inserted, i.e. have been inserted prior to start of the process 600. Once the video data is received at step 602, the process 600 can move to step 604 wherein a first image is captured with the endoscope at a first position. In one or more examples, the image captured at step 604 can be acquired using the techniques and methods described above with respect to step 304 of process 300 in FIG. 3. In one or more examples, the surgeon can position the endoscopic device to a desired location before capturing the image. As described further below, in order to use the structure-from-motion process to acquire depth information (so as to generate a three-dimensional model of the surgical space) two images acquired at different positions within the surgical space will be required so that the structure-from-motion process can be used to acquire accurate depth information.

Once the first image is acquired at step 604, the process 600 can move to step 606 wherein a second image is acquired with the endoscope at a second position that is different from the first position. The user can move the endoscope to a different position and then acquire an image from the video using the same techniques and methods described above with respect to step 304 of process 300 in FIG. 3. The structure-from-motion technique can depend on the motion parallax between two images of the same space taken from two different positions within the space in order to generate depth information about the space. Thus, in order to generate the required motion parallax between the two images to generate depth information, the user can move the endoscopic imaging device to a new position that is different from the first position so that the motion parallax between the two images is sufficient to generate depth information.

Once the second image is acquired at step 606, the process 600 can move to step 608 wherein a determination is made as to whether there is sufficient motion between the two images acquired at steps 604 and 606 so as to generate accurate depth information using the structure-from-motion process. As described above, sufficient motion parallax between the two images is required so that accurate depth information can be generated. Thus, a determination can be made as to whether the motion between the two images is sufficient to perform the structure-from-motion technique. If there is not sufficient motion as determined at step 608, the user can be notified and the process can revert back to step 604, wherein the user can acquire a new set of images with sufficient motion between them to perform the structure-from-motion process for acquiring depth information.

If it is determined that there is sufficient motion between the images at step 608, the process 600 can move to step 610 wherein the structure-from-motion process can be applied to the images acquired at step 604 and step 606 to generate depth information. The structure-from-motion process can include finding corresponding features from each image and tracking those features from one image to the next. Once the features from each of the images acquired at step 604 and 606 are matched, the structure-from-motion process can use the feature trajectories over time to reconstruct their three-dimensional positions and acquire depth information.

Once the structure-from-motion process is applied to the images at step 610, the process 600 can move to step 612 wherein the depth information acquired by the structure-from-motion process is used to generate a three-dimensional of the surgical space as described above with respect to FIG. 3.

The three-dimensional model generated using the systems and methods described above can be used to provide a surgeon with accurate three-dimensional measurements using endoscopic imaging data taken in a surgical cavity during a minimally invasive procedure. As described in further detail below, the user can mark various points in an endoscopic image, and using the three-dimensional model (and the size information derived from the fiducial), the system can accurately measure one or more geometric relationships between the points that take into account the precise geometry and size of the surgical space based on the generated three-dimensional model.

Figure 7:
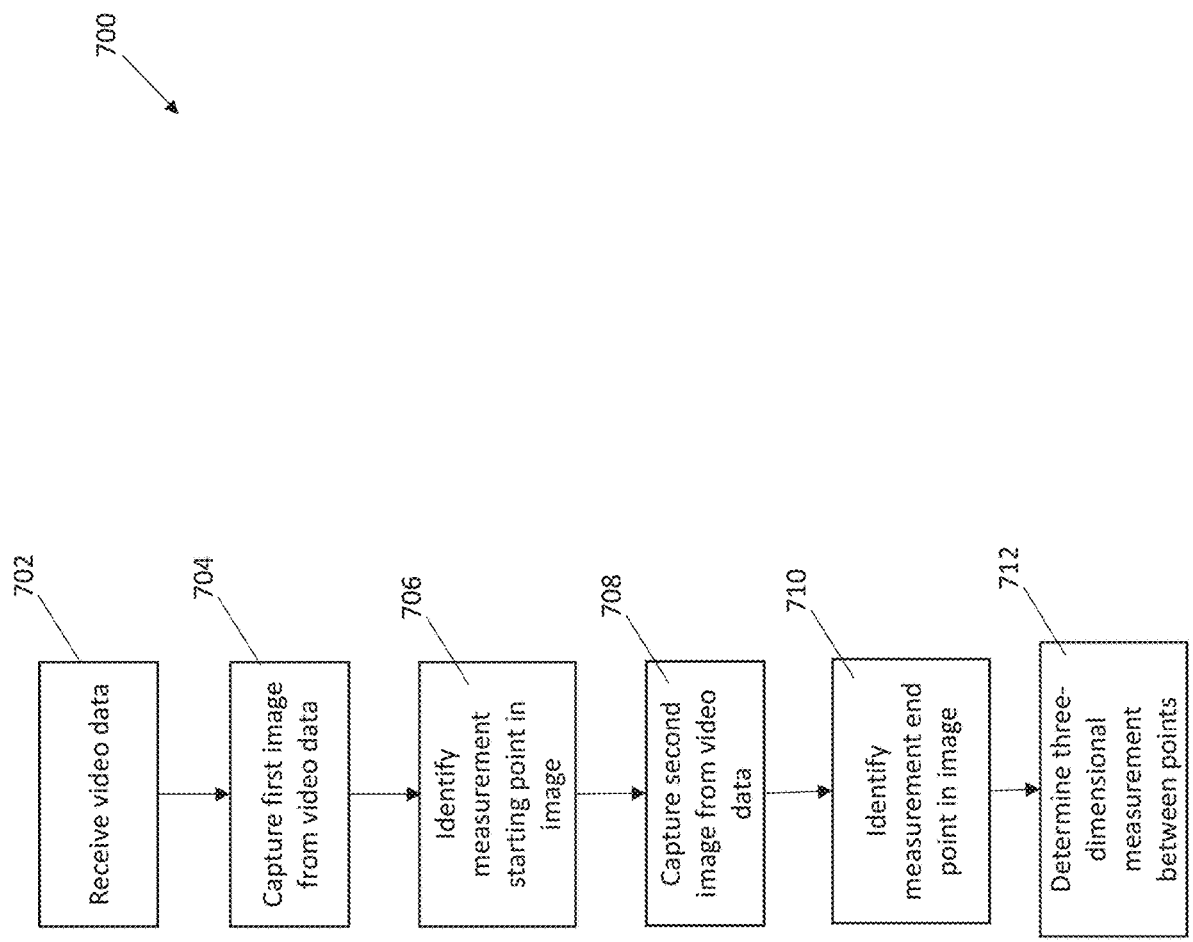
FIG. 7 illustrates an exemplary method for generating a three-dimensional measurement in a surgical field according to examples of the disclosure.

FIG. 7 illustrates an exemplary method for generating a three-dimensional measurement in a surgical field according to examples of the disclosure. The process 700 can begin at step 702 wherein video data is received from the endoscopic imaging device similar the method described above with respected to step 302. The endoscopic imaging device can be pre-inserted prior to start of the process 700. Once the video data is acquired at step 702, the process 700 can move to step 704 wherein a first image is captured using the video data. The first image can be captured by the surgeon using similar methods and techniques described above with respect to step 304 of FIG. 3.

Once the first image has been acquired at step 704, the process 700 can move to step 706 wherein a first measurement starting point can be identified in the captured image. The user can indicate the starting point of a measurement by engaging with a graphical user interface that includes the image. The user can "tap" a point on the image where they desire the start point of the measurement to be (e.g. on a touch screen of the system). The image acquired at step 704 can include a visualization of a surgical tool that can be used by the user to indicate where to begin a three-dimensional measurement. As will be described below, the visualization of the tool in the image can be used to determine a start point for a measurement. As an example, the user can place a pointer tool at a desired location to start a measurement and then acquire an image once the pointer is at the desired location. As will be described in detail below, the systems and methods described herein can determine the exact position of a distal end of the pointing tool and mark that point as the starting point for a measurement. Oher tools can be used to indicate a starting point for a measurement such as a drill guide, a shaver, a radio frequency (RF) probe, or any endoscopic tool with a rigid component.

Once the starting point of the measurement has been identified at step 706, the process 700 can move to step 708 wherein a second image can be captured from the endoscopic video data. The second image of step 708 can be acquired using the same techniques described above with respect to step 704. Once the second image is captured at step 708, the process 700 can move to step 710 wherein an end point can be identified in the image. Similar to the example of step 706, the end point can be identified by the user directly by providing the user with a graphical user interface that includes the second image, and allowing the user to tap the part of the image they want the end point of the measurement to be at. Additionally or alternatively, the image acquired at step 708 can include a visualization of a surgical tool that can be used by the user to indicate where to begin a three-dimensional measurement. As will be described below, the visualization of the tool in the image can be used to determine an end point for a measurement. As an example, the user can place a pointer tool at a desired location to end the measurement and then acquire an image once the pointer is at the desired location. As will be described in detail below, the systems and methods described herein can determine the exact position of a distal end of the pointing tool and mark that point as the end point for a measurement. The user can indicate the starting and end points of a measurement using a "press and hold" technique. In one or more examples, the press and hold technique can refer to a process in which the user initially presses a button located on the pointer tool to indicate the start point of a measurement, and can keep the button pressed down while drawing a shape (such as a line, curve, circle, etc.). The user can let go of the button to indicate the end point of the measurement. Measurements can be taken periodically while the user is pressing the button on the tool, so as to give intermediate measurements while a particular line is being drawing to indicate the current size of the line or shape being drawn.

Rather than placing the endpoints of a measurement on two separate images, the two endpoints can be placed on the same image such that when the starting point of a measurement is indicated by the user, the system can freeze the frame and allow the user to place the end point of the measurement on the same still image captured by the system. A user can draw a shape, and the system can approximate the shape that was intended by the user. For instance, the user can free draw a circle, and the system can modify the user's free drawn circle with a geometrically accurate circle, thus not requiring the user to draw perfectly proportioned or sized shapes.

Rather than having the end point of a measurement be indicated by the user, additionally or alternatively, the end point can automatically detected. For instance, if a user is trying to avoid certain nerves or other anatomical features in the internal area in the patient, then the systems and methods described above can be used to measure the distance that a tool is from a sensitive portion of the patients anatomy and the user can be alerted if the tool is coming within a pre-determined threshold distance from the sensitive anatomy. Thus, using the process 700 of FIG. 7, step 706 can include identifying the tip of a tool in an image using one or more methods described within the present disclosure. At step 710 the end point can be identified by locating a particular anatomical feature of the patient. For instance, an anatomical feature can be fluoresced (i.e., have a fluorescent dyeing agent applied to it) such that the anatomical structure can be identified by an image processing unit using one or more computer vision processes. For instance, a patient's nerves or blood vessels can be fluoresced so that they can be easily identified (i.e., the contours of the nerve can be identified so that they can be avoided). The computer vision process can be utilized to determine the end point in a measurement. For instance, the end point of the measurement identified in step 710 can represent the closest point of the anatomical structure to the starting point of the measurement identified at step 706. Additionally or alternatively, one or more machine learning models can be used to identify the contours of an anatomical feature, so as to identify an end point of the measurement. The one or more machine learning models can be trained using fluoresced images of the anatomical feature to be identified, and thus may not require that the actual anatomy of the patient be fluoresced in order to identify the anatomy in the surgical imaging data.

Once the end point of the measurement has been identified at step 710, the process 700 can move to step 712 wherein a three-dimensional measurement can be calculated using the start point established at step 706, the end point established at step 710, and a three-dimensional model of the surgical space (and fiducial size information) may be generated using the methods and techniques described above with respect to FIGS. 3-6 above.

Figure 8:
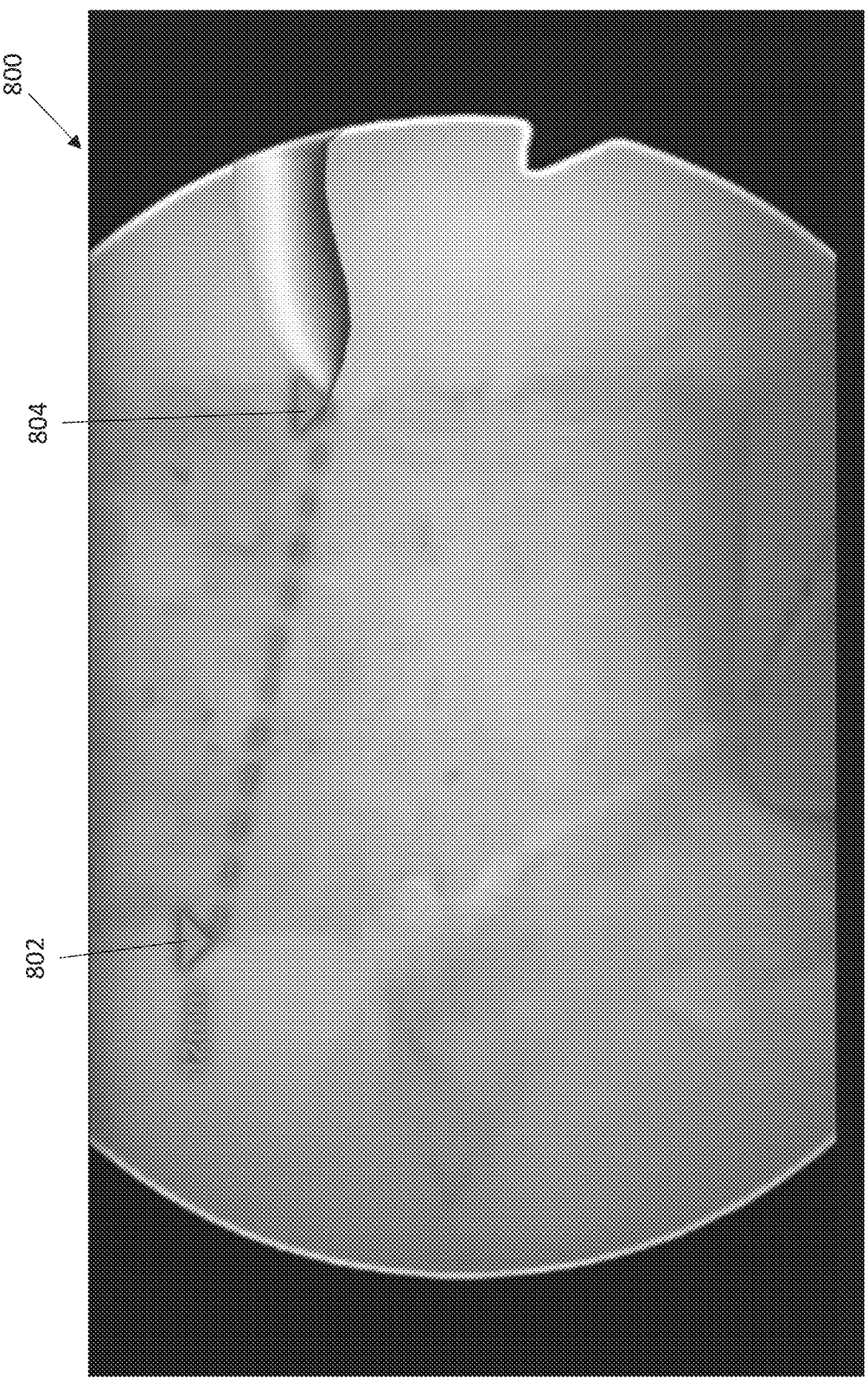
FIG. 8 illustrates an exemplary three-dimensional measurement using the exemplary systems and methods described herein according to examples of the disclosure.

The example provided above with respect to FIG. 7 can be used to measure the three-dimensional between two points in the surgical space. FIG. 8 illustrates an exemplary three-dimensional measurement using the exemplary systems and methods described herein according to examples of the disclosure. The image 800 illustrated in FIG. 8 can include a start point for the measurement as marked at 802. An image can be shown to the user that indicates the precise location in the image where the start point is. In the example of FIG. 8, the user can place the pointer tool at the end point of the measurement as shown at 804. Using a three-dimensional model of the surgical space as well as the size information provided by the fiducial marker, the system can determine the three-dimensional distance between the start point 802 and the end point 804 (which in the example in the figure is indicated as being 12 mm).

Figure 9:
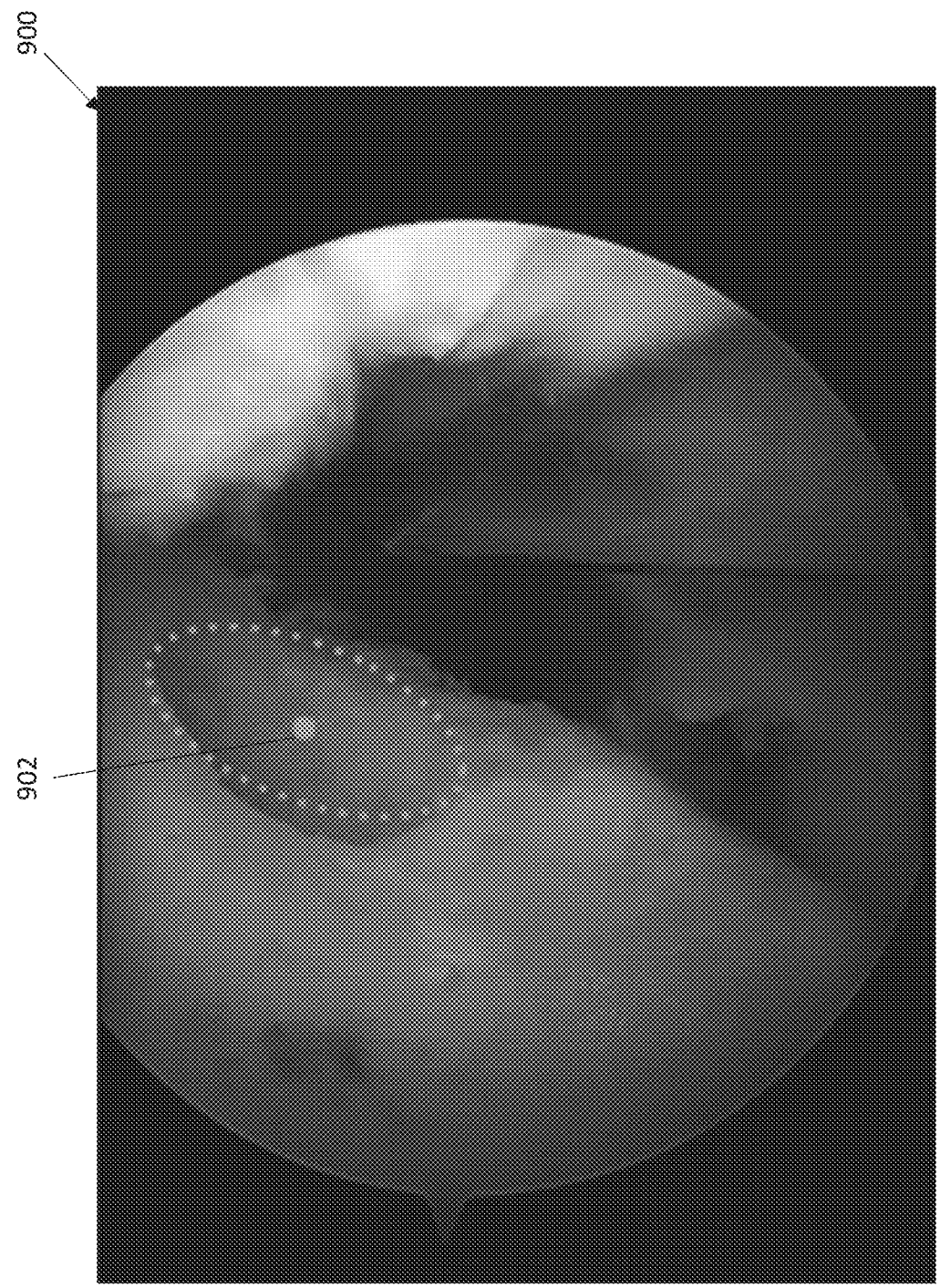
FIG. 9 illustrates another exemplary three-dimensional measurement using the exemplary systems and methods described herein according to examples of the disclosure.

The techniques and process described above with respect to FIG. 7 can also be applied to other types of geometric measurements. FIG. 9 illustrates another exemplary three-dimensional measurement using the exemplary systems and methods described herein according to examples of the disclosure. In the example of FIG. 9, the user can indicate the start point of a measurement as indicated at 902 in the image 900. Using the three-dimensional model and the fiducial information, the system can determine a circular area of a pre-determined dimension around the point 902, with point 902 serving as the center of the circle. In the example of FIG. 9, the process may only require that one measurement point be specified (rather than two as shown in FIG. 7). The user can mark the point 902 using the techniques described above with respect to FIG. 7, and then specify the radius of the circle to be drawn. Using the three-dimensional model previously generated, the system can calculate the circumference of the circle and display a visual representation of the circle with the pre-specified area on a graphical display provided to the user during the minimally invasive surgical procedure.

Figure 10:
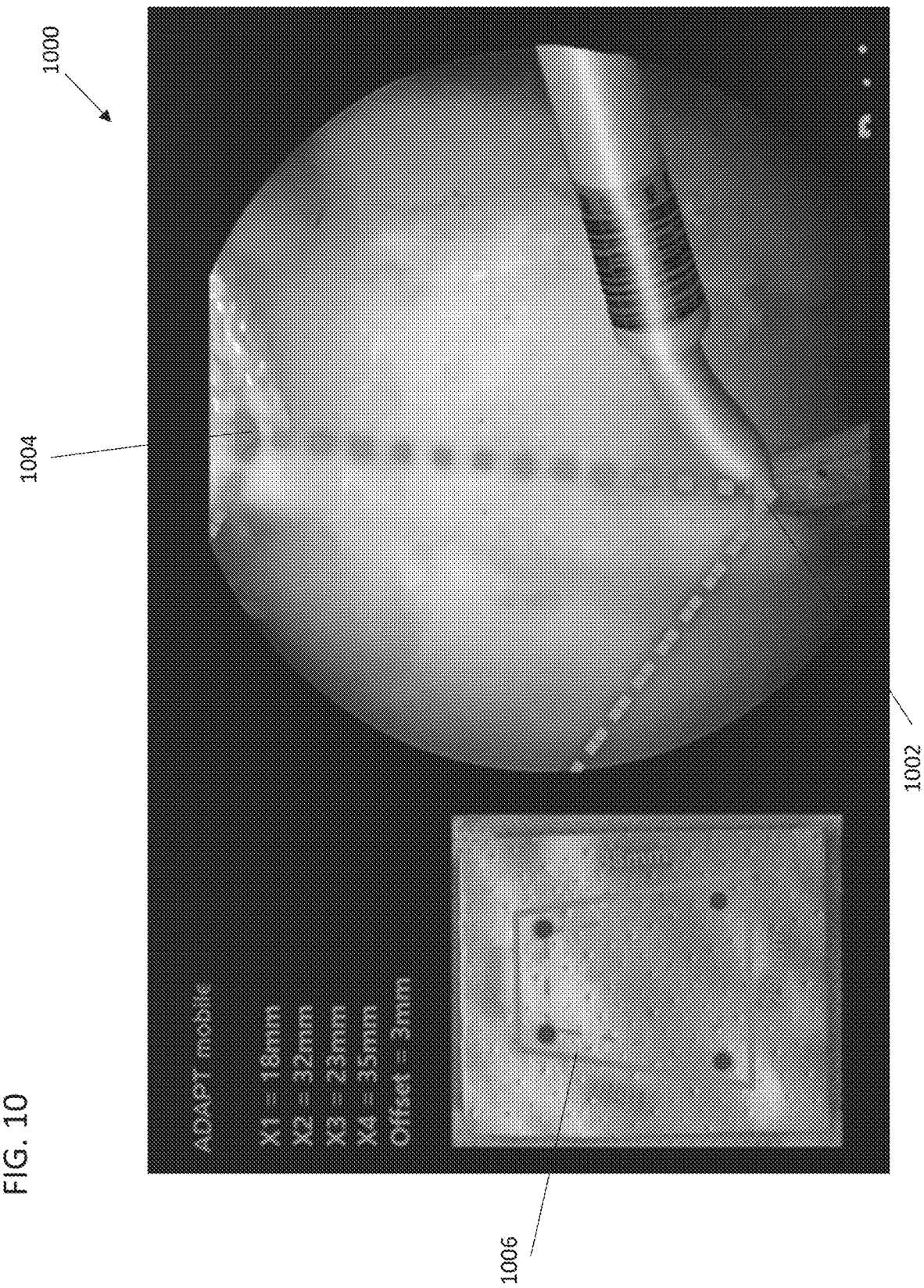
FIG. 10 illustrates another exemplary three-dimensional measurement using the exemplary systems and methods described herein according to examples of the disclosure.

The process 700 can be used to define a plane and take a measurement of the area of the plane using a three-dimensional model of the surgical space as well as the size information acquired from the fiducial marker. FIG. 10 illustrates another exemplary three-dimensional measurement using the exemplary systems and methods described herein according to examples of the disclosure. In the example 1000 of FIG. 10, a user can mark a plurality of points in the surgical space (as indicated at 1002 and 1004). Once the user marks the plurality of points, those points can be used define a plane based on the identified points as shown at 1006 in the example 1000 of FIG. 10. The three-dimensional model of the surgical space as well as the fiducial size information can be used to calculate a three-dimensional area of the defined plane.

As discussed above, the points to be used in a measurement can be set by positioning a tool (such as a pointing tool) at the location where the point is to be established. But the task of determining a point based on the position of a tool can present its own challenges. For instance, in the example of a pointing tool, a distal end of the pointing tool (i.e., the end point of the tool that makes contact with the tissue of the patient) may not be visible in image that captures the tool. For instance, the distal end of the pointing tool may be buried in the patient's tissue or dug into bone such that it is not visible in the image. Furthermore, the pointer tool may be anywhere in the image. It may enter view from outside the field of view of the scope, or it may enter the view of the camera through a cannula.

Figure 11:
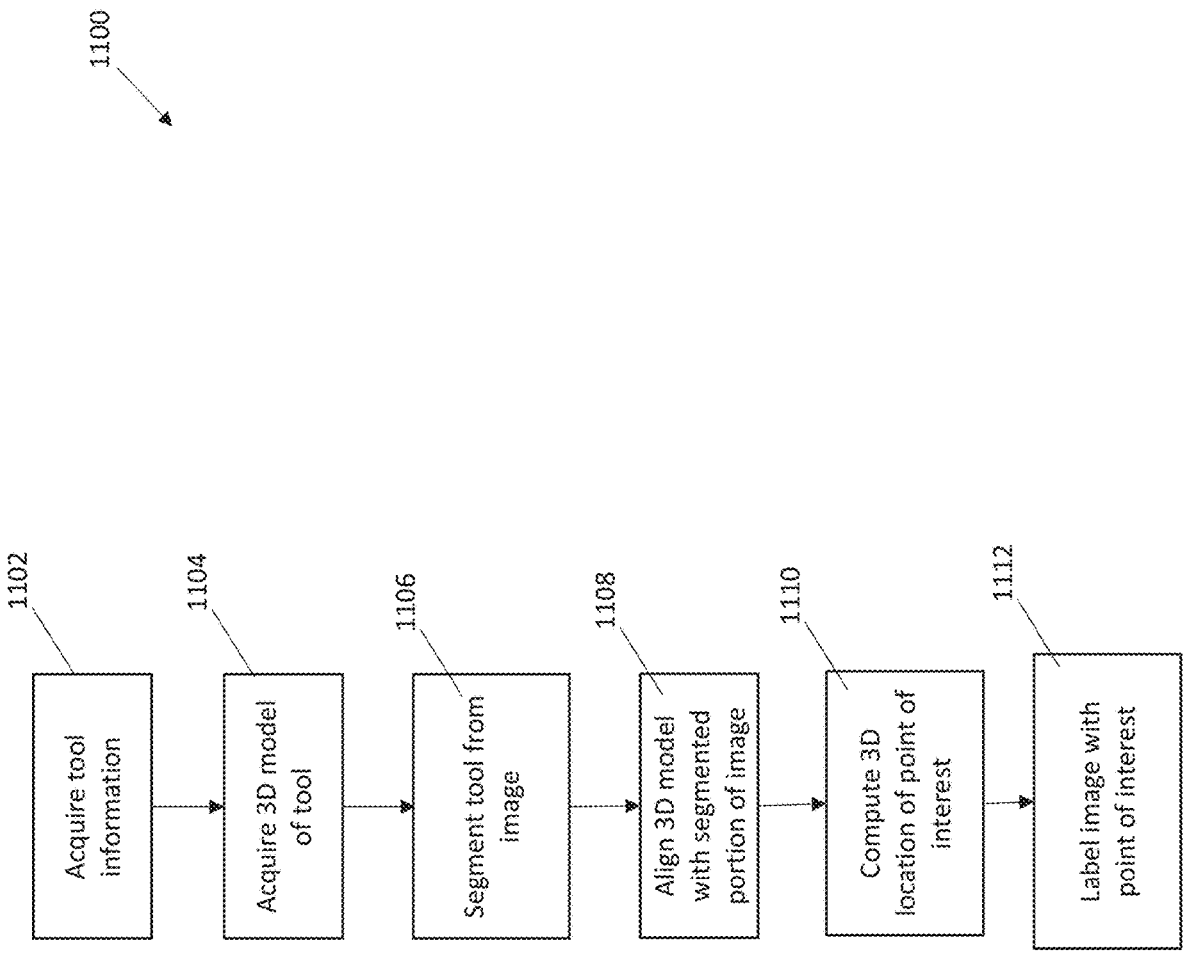
FIG. 11 illustrates an exemplary method for determining the position of a distal end of a tool in an image obtained from an endoscopic imaging device according to examples of the disclosure.

Thus, in in order to determine where to establish a measurement point in an image, a process for determining the position of a distal end of a tool can be implemented that utilizes a machine learning model to detect the location of a tool in an image, and then determines the position of the distal end of that tool so that a measurement point can be established at the precise location in an image where the distal end of the tool is located. FIG. 11 illustrates an exemplary method for determining the position of a distal end of a tool in an image obtained from an endoscopic imaging device. The process 1100 of FIG. 11 can begin at step 1102 wherein information about the tool that is being used to establish a measurement point can be acquired. The tool can include a plurality of barcodes laser marked onto them. These barcodes can indicate both a tool ID number (so that the tool can be identified from the barcode as well as a rough rotational estimate. For example, there may be six barcodes printed around the circumference of the device, which would provide approximate rotational orientation within 60 degrees. The system can determine the rotational orientation of the tool based on which barcodes of the device are visible. An image from the endoscopic imaging device can be processed by a barcode finding algorithm that can determine the presence of a barcode in the image, scan the barcode, and then use the acquired barcode to download information about the tool. The barcode finding algorithm can also determine a bounding box for where the barcode exists in the image.

Once the tool has been identified at step 1102, the process 1100 can move to step 1104 wherein a three-dimensional model of the tool can be acquired. The barcode acquired at step 1102 can be used to acquire the three-dimensional model. Additionally or alternatively, the tool ID acquired at step 1102 can be used to look up a three-dimensional model of the tool. The three-dimensional model of the tool can refer to a scaled representation of the tool in three dimensions, that as described in further detail below can be used to determine where the distal end of a tool in the surgical space is located so as to indicate a measurement point. The three-dimensional model of the tool can include metadata for the center point of the barcode region in the tool, the location of the central axis of the tool's shaft, as well as the point of interest (i.e., the point of the tool that identifies where to place the measurement marker). The point of interest can be found at the distal most end of the tool.

Once the three-dimensional model has been acquired at step 1104, the process 1100 can move to step 1106 wherein the portion of an image in which the tool appears is segmented from the image. Segmenting a tool from the image can include using one or more machine learning models to identify a tool in an image and to then identify the pixels in the image that belong to the tool. The one or more machine classifiers can be implemented using one or more convolutional neural networks (CNNs). CNNs are class of deep neural networks that can be especially configured to analyze visual imagery to determine whether certain features exist in an image. Each CNN used to generate a machine classifier can include one or more layers, with each layer of the CNN configured to aide in the process of determining whether a particular image includes a feature that the overall CNN is configured to determine. Alternatively or additionally, the CNNs can be configured as Region-based Convolutional Networks (R-CNNs) that can not only determine if a particular image contains a feature, but can identify the specific location in the image where the feature is shown. Additionally, the systems and methods described above can be implemented using other machine learning models such as U-Net CNNs and/or Deeplab Semantic Image Segmentation models. The machine learning model can be configured to identify the portion of image that includes a tool. In the case of segmentation or region based classifiers such R-CNNS, the machine learning model can be generated by using one or more training images that can be annotated on a pixel-by-pixel or regional basis to identify the specific pixels or regions of an image that contained a specific characteristic (such as the presence of a tool). For instance in the case of R-CNNs, the annotations can take the form of bounding boxes or segmentations of the training images. As will be discussed in further detail below, the one or more machine learning models can be generated using a supervised training method in which annotated training images are used to train the classifier to determine the pixels of an image associated with a tool. Additionally or alternatively, the machine learning models can be generated using semi-supervised, self-supervised, and/or unsupervised processes, or any combination thereof.

Specific features of the segmented portion of the image can be identified. For instance, to approximate the general direction that the tool is facing, a best fit line can be determined through all the points in the segmented portion of the image. In order to find the edges of the tools, the pixels of the segmented portion that do not have eight pixel neighbors can be selected.

Step 1106 can be used to identify the presence of a tool and identify which pixels of the image are associated with the tool. However, it may not identify the specific tool and thus may not be able to be used directly to find the distal end of the tool that will serve as the measurement marker in a three-dimensional measurement. However, since the tool has already been identified at steps 1102, in order to identify the distal end of the tool using the segmented portion of the images, the process 1100 can move to step 1108 wherein the 3D model of the tool acquired at step 1104 is aligned with the segmented portion of the image. By aligning the 3D model with the portion of the image that has been segmented (also referred to as a segmentation mask), the distal end of the tool can be precisely identified so as to identify where the measurement marker should be placed in relation to the location of the tool.

Aligning the 3D model of the tool with the segmentation mask can include aligning the center point from the bounding box (identified when the barcode is read) to the center point of the 3D model. Aligning the 3D model of the tool to the segmentation mask can include aligning the best fit line identified when the segmentation mask is identified (as described above) with the center line of the 3D model of the tool, and aligning the rotation of the 3D model of the tool about its own axis using the barcode information that describes the orientation of tool in the surgical space. Alignment of the 3D tool model and the segmentation mask can be done in the XYZ, UVW space. Aligning the 3D model with the segmentation can include iteratively varying the XYZUVW and scale parameters, and comparing the fit of the model of the edges by projecting the 3D model into the scene taking account for the intrinsic optics of the scope. For each iteration of the process of aligning the 3D model, a silhouette of the model can be determined and compared with the identified edges of the mask. A score for each iteration can be computed based on the fit between the segmentation mask and the 3D model, and once the iterations are complete, the fit with the best score can be selected.

Once the 3D model of the tool has been aligned with the segmented portion of the image at step 1108, the process 1100 can move to step 1110 wherein the three-dimensional location of the point of interest (i.e., the measurement marker) can be identified based on the alignment of the 3D model of the tool with the segmentation mask. As discussed above, the 3D tool model can include metadata that identifies the location on the tool that is to correspond to the point of interest. Thus, after the 3D model of the tool has been aligned with the segmentation mask, the location of the point of interest can be identified in the image and a measurement marker can be placed at that point. Thus, once the point of interest has been identified at step 1110, the process 1100 can move to step 1112 wherein the image is labeled with a measurement marker that corresponds to the determined point of interest.

Figure 12:
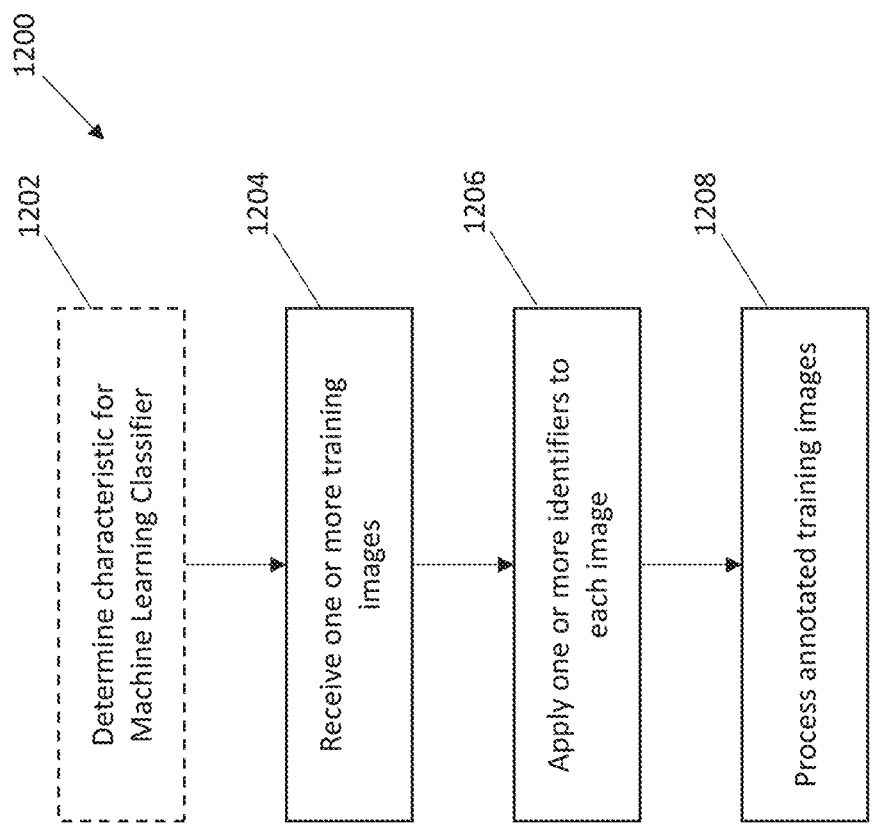
FIG. 12 illustrates an exemplary method for annotating images according to examples of the disclosure.

As described above, segmenting an image to find the pixels of the image associated with a tool can utilize one or more machine learning models that is configured to identify pixels of an image associated with a tool. The one or more machine learning models can be generated using a supervised learning process in which training images are annotated with the features shown in the training image so as to train the classifier to identify those same features in other images presented to the classifier. FIG. 12 illustrates an exemplary method for annotating images according to examples of the disclosure. In the example of FIG. 12, the process 1200 can begin at step 1202 wherein a particular characteristic for a given machine learning model is selected or determined. The characteristics can be selected based on the conditions that can be used to identify the portion of an image that contains a tool that can be used to establish a measurement marker, influence the inflow, outflow, and/or pressure requirements of a surgical pump during a surgical procedure. Step 1202 can be optional, as the selection of characteristics needed to for the machine learning models can be selected beforehand in a separate process.

Once the one or more characteristics to be classified have been determined at step 1202, the process 1200 can move to step 1204 wherein one or more training images corresponding to the selected characteristics are received. Each training image can include one or more identifiers that identify the characteristics contained within an image. The identifiers can take the form of annotations that are appended to the metadata data of the image, identifying what characteristics are contained within the image. A particular image of the training image set can include multiple identifiers.

If the training images received at step 1204 do not include identifiers, then the process can move to step 1206 wherein one or more identifiers are applied to each image of the one or more training images. The training images can be annotated with identifiers using a variety of methods. For instance, the training images can be manually applied by a human or humans who view each training image, determine what characteristics are contained within the image, and then annotate the image with the identifiers pertaining to those characteristics. Alternatively or additionally, the training images can be harvested from images that have been previously classified by a machine classifier. For instance, an image that has been previously identified as including a tool can be annotated with the identified characteristics (i.e., annotated with one or more identifiers) and the image can then be transmitted to and stored in a memory for later use as a training image. In this way, each of the machine learning models can be constantly improved with new training data (i.e., by taking information from previously classified images) so as to improve the overall accuracy of the machine learning model.

Instead of using real images to train the classifier, the training images can be synthetically created with engineered content or features for purposes of training the classifiers with an enlarged training set. Synthetic data allows for domain randomization that real data does not (i.e., it allows for changes to small details of the scene that would otherwise never be seen, which allows AI models to learn more salient features and generalize better). Some options for domain randomization include: changes in background lighting, changes in object positions, changes in object colors, textures, and scale, and changes in camera parameters. Multiple types of synthetic data can be used. For instance, artificial scope circles can be placed onto non-scope images to generate pixel perfect ground truth circle masks. Synthetic data can include engineered photos of tools in which three-dimensional models of production tools can be inserted into figures. Modeled objects with known three-dimensional geometries can be placed in a fixture, and the camera motion can be precisely controlled in four axes.

In the case of segmentation or region based classifiers such R-CNNS, the training images can be annotated on a pixel-by-pixel or regional basis to identify the specific pixels or regions of an image that contained a specific characteristics. For instance in the case of R-CNNs, the annotations can take the form of bounding boxes or segmentations of the training images. Once each training image has one or more identifiers annotated to the image at step 1206, the process 1200 can move to step 1208 wherein the one or more training images are processed by each of the machine learning models in order to train the classifier. In the case of CNNs, processing the training images can include building the individual layers of the CNN. The machine learning models can be generated using other training processes including semi-supervised and unsupervised processes. For instance, the machine learning models can be generated using such approaches as Bootstrap Your Own Latent (BYOL) self-supervised learning, SimCLR self-supervised learning, Simple Siamese Representation Learning ("SimSiam") unsupervised learning, and Swapping Assignments between Views ("SwAV") unsupervised learning techniques. The machine learning classifiers can be generated using a combination of supervised, semi-supervised, and unsupervised learning methods.

The process 1100 of FIG. 11 can be applied to specific procedures, such as surgical procedures, in which tools are used to measure distances within the internal portion of a patient. As an example, a "Roux-En-Y" surgical procedure requires the surgeon to take longer (10-100 cm) measurements of the stomach and small intestine with a set of graspers. For instance, the user may be required to measure multiple lengths along the small intestine to determine the correct location to join separated stomach and intestine segments. In order to take long measurements along the intestine, the user may make use of multiple graspers, and take the measurements in segments (rather than one long measurement), with both individual segments and running tally of the total measurement displayed to the user. The user may use the multiple graspers in a leader-follower motion, so that even though there are multiple segments, only two graspers are required. Thus, the user may use a first grasper and a second grasper to make a first measurement along the intestine. Once the first measurement is taken, the user can then move the first grasper to a position further along the intestine than the second grasper, and take a second measurement. Once the second measurement is acquired, the user can move the first grasper further along the intestine to acquire a third measurement, and so on and so forth. The process described above with respect to FIG. 12, can be used to acquire the tip or point of interest of the grasper, and can use the acquired tip or point of interest to mark the measurement points or segments measured by the surgeon during the roux-en-y procedure. Additionally or alternatively, the roux-en-y procedure can also take advantage of the camera motion determination techniques described in further detail below, to account for camera motion when measuring segments of the intestine or anatomy of the patient.

In the examples described above with respect to FIGS. 8-12, the user (e.g. surgeon or medical practitioner) is able to mark points of interest in a given image or video feed. The points of interest can establish measurements start points/end points, or more generally, any part of the anatomy that a user may want to track during a procedure, such as a surgical procedure, that involves imaging of the internal portion of a patient. When a user marks a point of interest, the user may want to track that point of interest throughout the surgery at any given moment in time. Thus, once the user establishes a point of interest on an image, that portion of the image can be marked with a graphical icon or flag (or some other type of graphical overlay) that points to the location specified by the user. The flag placed on the image by the user can be persistent, meaning that the flag can stay affixed to the anatomy or portion of the image marked by the user while the procedure is taking place. Thus, the graphical overlay used to indicate the point of interest can remain on the screen throughout the procedure to mark the point of interest throughout the duration of the procedure. Keeping the flag on the screen can be relatively straightforward when the camera or other imaging device within the internal portion of the patient is stationary. The graphical overlay (i.e., flag) simply keeps its position on the screen.

Figure 13:
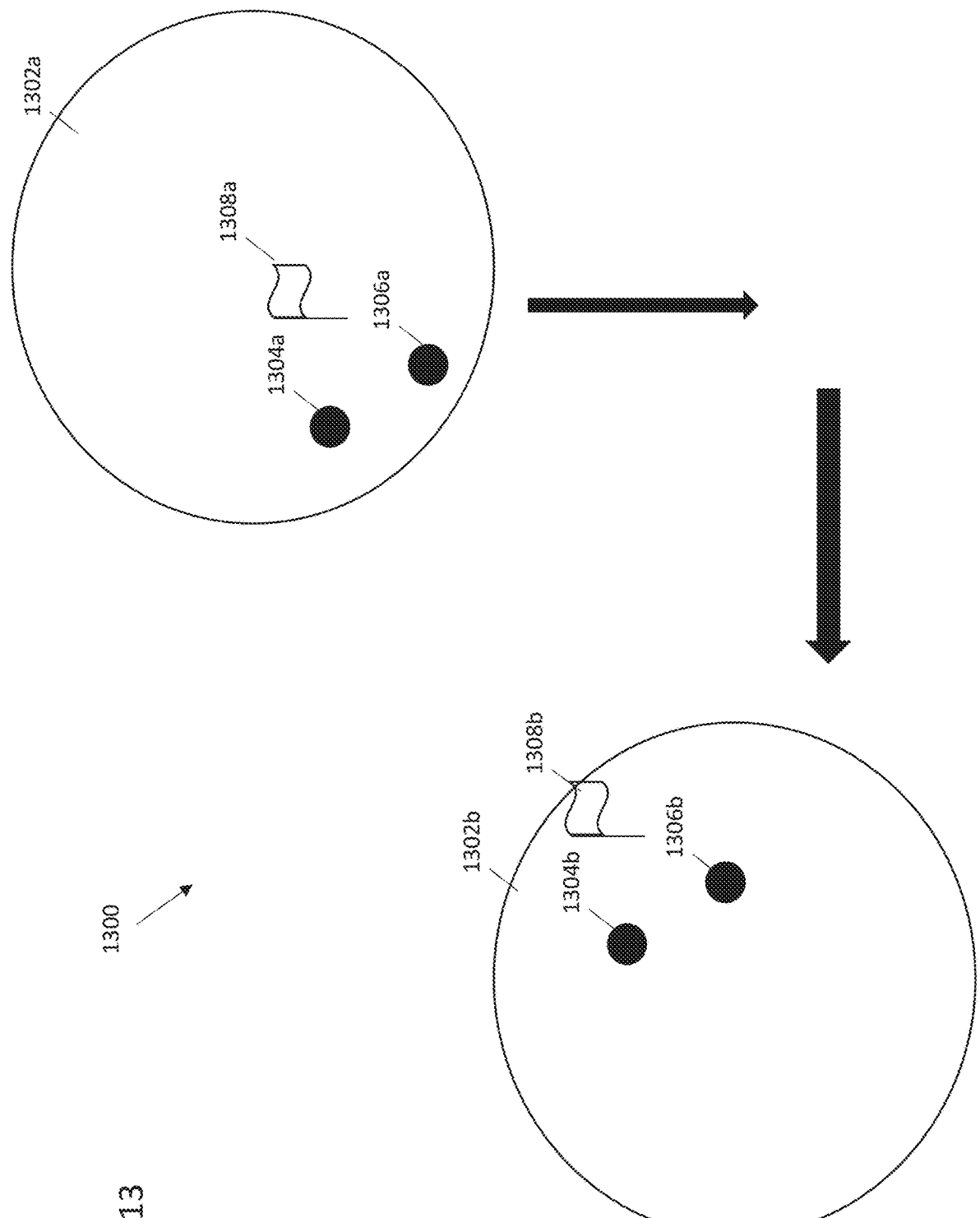
FIG. 13 illustrates an exemplary graphical overlay scheme for a point of interest in an endoscopic image according to examples of the disclosure.

However, if the camera is moving, then making sure that the flag on the screen corresponds to the location in the anatomy identified by the user can be challenging because the flag will be required to move on the screen so that it appears to be stuck to the anatomy when the camera moves. This can require a system to determine the amount and direction of movement and move the flag accordingly so that the flag corresponds to the anatomy or point that the user indicated. FIG. 13 illustrates an exemplary graphical overlay scheme for a point of interest in an endoscopic image according to examples of the disclosure. The example 1300 of FIG. 13 can illustrate two separate frames 1302*a* and 1302*b* of a medical imaging device video feed that is viewed by a user during a medical procedure. Frame 1302*a* of the example 1300 of FIG. 13 can be taken earlier in time than frame 1302*b*. Frame 1302*a* can include multiple features of interest 1304*a* and 1304*b*, which as described further below, can be identified in the frame for the purposes of determining camera movement. The frame 1302*a* can also include a flag 1308*a*. Flag 1308*a*, can represent a graphic that is overlaid over the frame 1302*a* in response to a user of the medical imaging device indicating a selection or portion of the internal portion of the patient they want to mark. Thus, while features of interest 1304*a* and 1304*b* represent parts of the anatomy that are visible within the video data, flag 1308*a* represents a feature that is added by a user, such as a surgeon or medical practitioner, to the video data after the video data has been received.

If the camera used to record frame 1302*a* remains stationary throughout the procedure, then features of interest 1304*a* and 1304*b*, as well as flag 1308*a*, can maintain their position within the frame throughout the procedure. However, if the camera moves during the procedure, then the position of features 1304*a* and 1304*b*, as well as flag 1308, will move within the frame, based on the direction and distance that the camera is moved. For instance, as shown in FIG. 13, frame 1302*b* can represent a frame of video that would appear if the camera used to obtain frame 1302*a* is moved down and to the left. In such an example, the position of features 1304*a* and 1304*b* of frame 1302*a*, will appear further down and to the left in the frame as illustrated by features 1304*b* and 1306*b* of frame 1302. Likewise, flag 1308*a* of frame 1302 will also appear further down and to the left as shown in frame 1302*b* by flag 1308*b*.

As described when a medical imaging device moves during a, e.g. surgical, procedure, the features visualized by the device will move according to the distance and direction of the movement. However, a graphical feature such as the flag 1308 of FIG. 13 may not conventionally automatically move with the movement of the camera, because the graphical feature is not part of the raw video data acquired from the imaging device. Thus, if a user uses a flag (or other graphical overlay) to mark a point of interest in a frame of video data, and then moves the video camera, a process is required to move the flag such that the flag appears "stuck" to the anatomy throughout the moving field of view of the video camera. The processed placement of the flag when the camera moves is such that the flag appears to point to the same point in the anatomy of the patient no matter where the camera moves.

Figure 14:
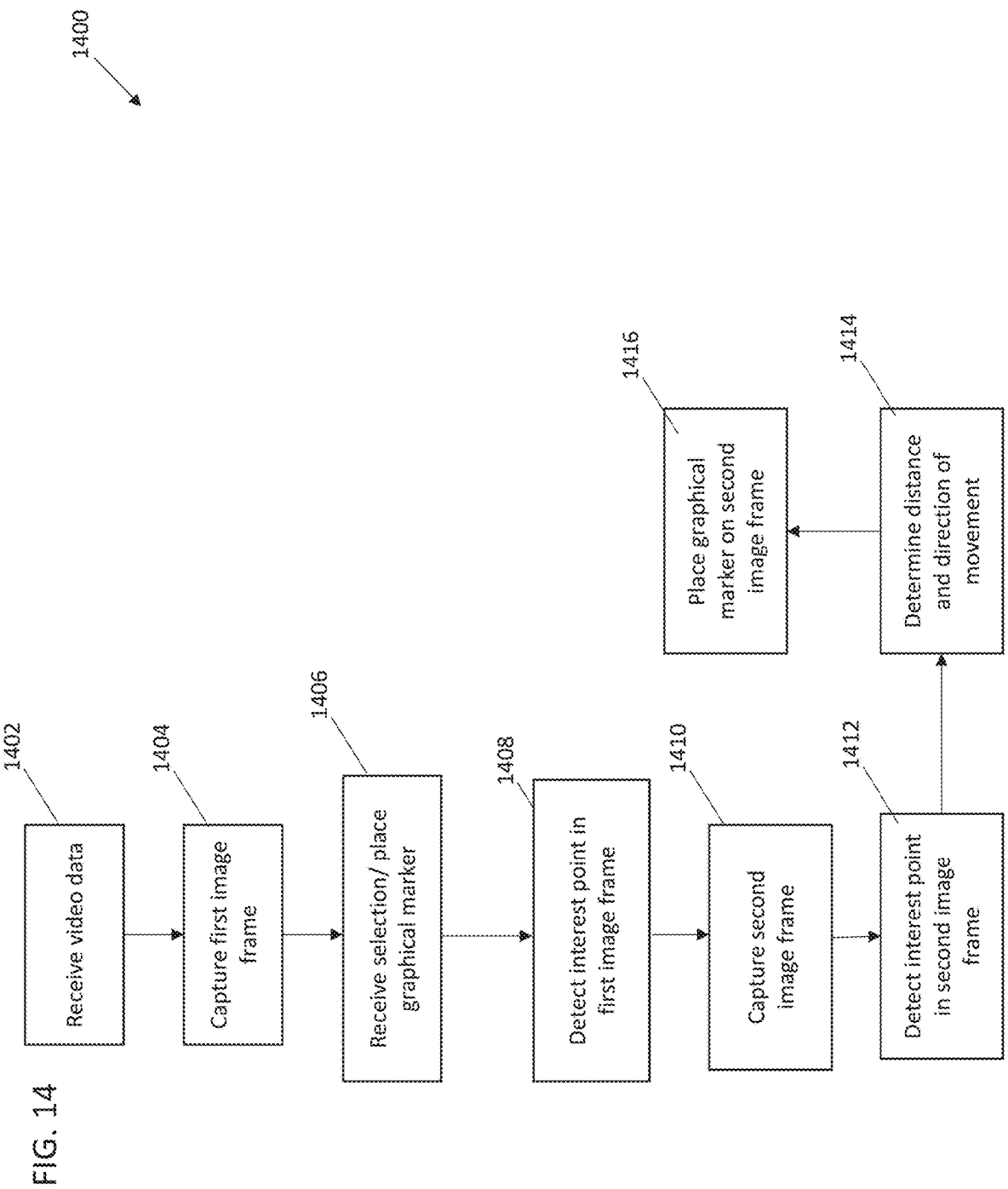
FIG. 14 illustrates an exemplary process for tracking the position of a graphical overlay in response to camera movement in video data according to examples of the disclosure.

FIG. 14 illustrates an exemplary process for tracking the position of a graphical overlay in response to camera movement in video data according to examples of the disclosure. The process 1400 can begin at step 1402 wherein the video data from a medical imaging device (such as an endoscopic camera) is received for viewing by a surgeon or other medical practitioner during a surgery or other medical procedure. The endoscope can be pre-inserted prior to start of the process 1400. Once the video data is received at step 1402, the process 1400 can move to step 1404 wherein a first image frame is captured from the video data. The "capturing" of image frames at step 1404 can include capturing one or more two-dimensional still images from the video data (i.e., generating and storing a screen shot of the video data). The images can be captured at step 1404 based on an indication or signal provided by the user to capture the one or more images. Alternatively or in addition to the examples described above, capturing a first image from the video data can be done automatically without indication from the user or without any prompting by the user. Capturing the first image frame at step 1404 can be prompted by the user indicating that they wish to select or place a flag or other graphical marker at a location within the internal portion of the patient imaged by the video data received at step 1404.

The process 1400 at step 1406 can also receive a selection of a point in the anatomy of the patient visualized in the video data received at step 1402 from a user of the system. As described above, the selection can initiate the capture of the first image frame at step 1404, and the image frame captured at step 1404 can be presented to the user so that they can mark the point in the anatomy of the patient that they want to flag or mark. Also at step 1406, the process can place a flag or other graphical marker (such as a graphical pin or arrow) at the point in the anatomy selected by the user. For instance, as shown in FIG. 13, a flag 1308a and 1308b can be placed as an overlay on the image frame in response to the user selecting a point in the anatomy that they wish to mark.

Once the point in the anatomy has been selected and a flag placed at the selected point at step 1406, the process 1400 can move to step 1408 wherein a point of interest in the anatomy visualized in the first frame captured at step 1404 can be detected. As described above, the flag placed by the user may not actually be at an identifiable point in the anatomy and furthermore may not be a point that can be used to track the motion of the camera, and thus at step 1408, the raw video data or processed video data (processed for clarity) can be used to identify a point of interest in the image that can be used to track camera motion. The process 1400 at step 1408 can identify one or more points of interest in the image frame. The points of interest can be identified using one or more machine learning models that are configured to detect interest points in images for use in computer vision applications such as the Greedily Learned Accurate Match Points (GLAM) keypoint detector, the Self-Supervised Interest Point Detector (Superpoint), Magicpoint, Unsuperpoint, or other machine learning models configured to learn match correspondences in images with known homographic transformations. The machine learning model or models used to detect points of interests (i.e., keypoints) in an image can be configured to extract stable points in an image that can be used to track the motion of a camera and determine the rotation and motion of a camera based on how those points move in a video feed based on the movement of those points in a subsequent frame of the image.

Once the one or more interest points are detected in the first image frame captured at step 1408, the process 1400 can move to step 1410 wherein a second image frame is captured from the received video data. The second video frame can be later in time than the first frame, and as described in further detail below can be used to determine whether and the extent to which the camera used to capture the video data has moved between when the first frame was captured and when the second frame was captured. Once the second frame has been captured at step 1410, the process 1400 can move to step 1412 wherein the interest points detected at step 1408 can be also detected in step 1412 using one or more of the machine learning models described above with respect to step 1408. If the camera has moved between capture of the first frame and capture of the second frame, then the interest points (or keypoints) located in the first frame will have moved to a different location in the image frame based on the extent and direction of the motion. As described in further detail below, the movement of the interest points can be used to determine where to place the flag in the second frame so that the flag appears stuck to the anatomy and moves according to the motion of the camera so that the flag points to the same location on the anatomy of the patient despite the motion of the camera.

Once the interest points are detected at step 1412, the process 1400 can move to step 1414, wherein the distance and direction of movement of the camera can be determined based on the movement of the interest points in the second captured image frame. The distance and direction of the movement of the camera can be calculated using homography, a computer vision technique that can be used to produce a motion matrix that indicates how much each pixel in the image has moved from a previous image using one or more homographic transformations. At step 1414, the frames captured at step 1404 and step 1410 can be matched using a k-nearest neighbors (KNN) algorithm with filtering that can be used to match the interest points identified in the first captured image with the interest points identified in the second captured image. From the matched correspondences, the estimation of motion can be performed using homography.

Once the amount of motion is estimated at step 1414, the process can then move to step 1416 wherein the flag (or other graphical marker) is placed on the second image frame in accordance with the estimated motion of the camera so that the flag points to the same point in the anatomy as it did in the first captured image. If the amount of motion determined between the first captured frame and the second captured frame is such that the flag position at the first captured frame no longer appears in the image, then the process 1400 at step 1416 can instead place a marker at the edge of the frame indicating a general direction of the flag.

In subsequent frames, if the movement of the camera is such that the anatomy pointed to by the flag reappears in the image, then the flag can be reapplied at the point in the anatomy indicated by the user.

In addition to tracking flags, the camera motion estimation techniques described above can have further applications. For instance, the motion tracking using homography can be useful in image stitching (i.e., combining multiple frames/images into one larger image covering more area). The area that can be viewed in a frame is limited by the field of the view of the camera or imaging device used to collect the video data that is used to generate a frame. Thus, a user may only be able to visualize a limited portion of the anatomy or internal portion of a patient at any given time, since a single frame of video data will be limited to the portion of the anatomy that appears within the field of view of the camera. However, multiple frames of a video (i.e., multiple images) taken when the camera is at different positions within the anatomy can be combined together to form a larger image such that the surgeon can view a larger portion of the anatomy in a single image. However, stitching together pictures so that the resultant image forms a larger image requires knowledge of the motion of the camera so that the image can be "stitched" at the right locations to form an accurate image of the internal portion of the patient. In other words, the location at which two images are to be combined to form a larger single image can be dependent on the extent and direction of the camera movement between the first image and the second image. If the location at which two images are combined is not commensurate with the amount of camera motion between the two images, then the resultant image made from combining the two images will appear distorted or will provide an inaccurate representation of the anatomy of the patient.

The above concept of stitching images together to form larger images can also be employed to create three dimensional models of a patient's anatomy. As described above with respect to FIGS. 3-6, depth information can be acquired for each captured frame from video data so as to acquire one or more three-dimensional images from one or more two-dimensional images. However, each three-dimensional image faces the same limitations of a two-dimensional image acquired by a medical imaging device insofar as the field of view of the image (i.e., the size of the portion of the anatomy shown in the image) will be limited by the field of view of the device used to produce the image. Thus, the three-dimensional images acquired above using the processes described with respect to FIGS. 3-6 can also be combined (i.e., "stitched") together to form larger single images, and thus can be used to generate three-dimensional models of the patient's anatomy.

Figure 15:
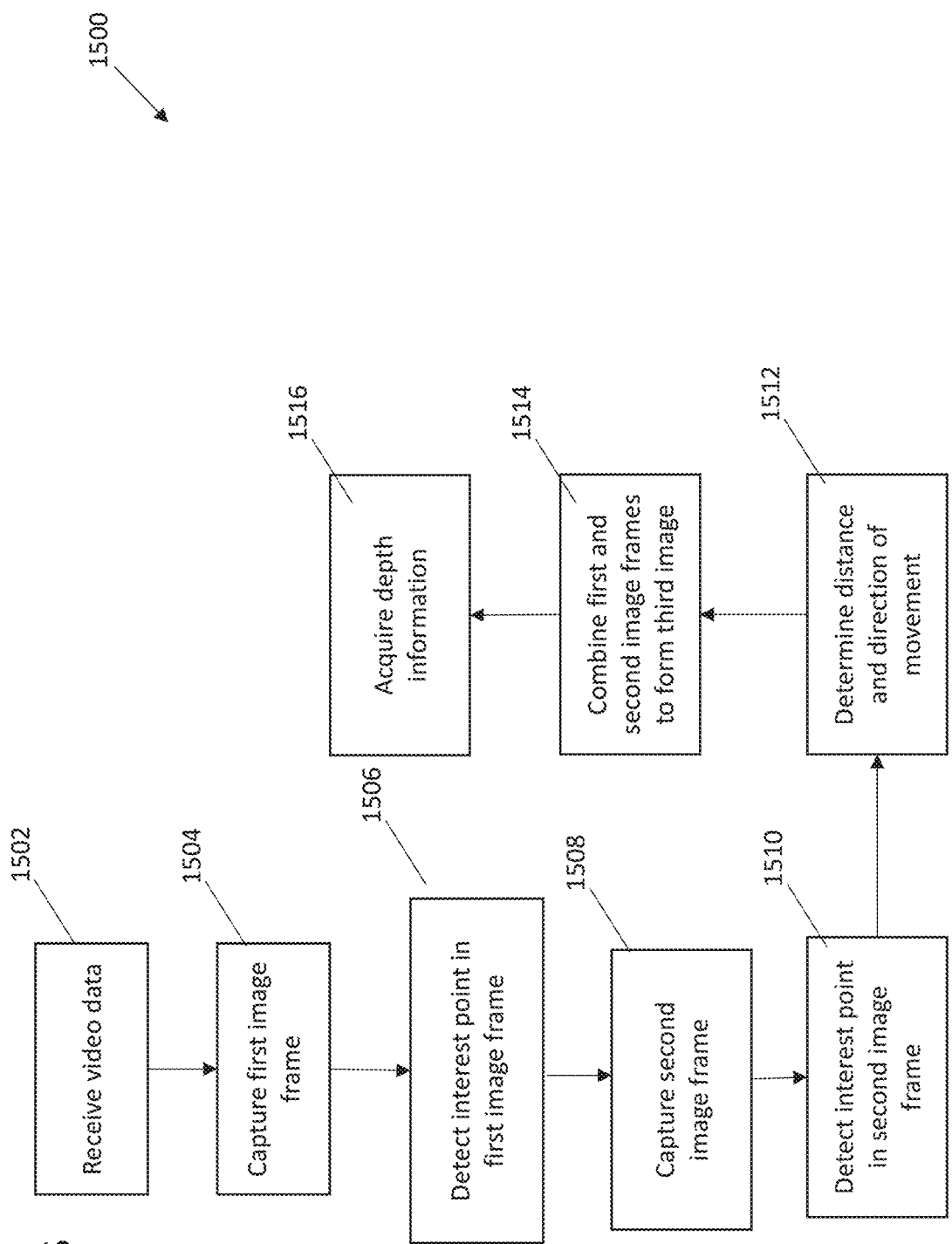
FIG. 15 illustrates an exemplary process for generating a three-dimensional model from a plurality of three-dimensional images according to examples of the disclosure.

FIG. 15 illustrates an exemplary process for generating a three-dimensional model from a plurality of three-dimensional images according to examples of the disclosure. The process 1500 of FIG. 15 can begin at step 1502 wherein video data is received from a medical imaging device. The process of receiving the video data can be substantially similar to the processes for receiving video data described above with respect to FIGS. 3, 6, 7, and 14, and thus a discussion of those figures can be referenced for details on how video is received at step 1502 of FIG. 15. Once the video data has been received at step 1502, the process 1500 can move to step 1504 wherein a first image frame is captured. Step 1504 of process 1500 can be substantially similar to step 1404 of FIG. 14, insofar as the process of capturing the image. Once the first image is captured at step 1504, the process can move to step 1506 wherein a first interest point (i.e., keypoint) is detected in the first image in a manner that is substantially similar to step 1408 of FIG. 14. As described above with respect to step 1408, the interest point detection can include using one or more machine learning models to determine one or more interest points in the image that can be later used to determine motion of the camera between frames.

Once the interest points for the first captured frame are determined at step 1506, the process 1500 can move to step 1508 wherein a second image frame is captured from the video data received at step 1502. In a manner substantially similar to step 1410 of FIG. 14, the second captured image can be captured after the first image and represent an image of the patient's anatomy after the camera has moved. Once the second image has been captured at step 1508, the process 1500 can move to step 1510 wherein the interest points within the second image are determined in substantially the same manner as step 1412 of FIG. 14. Once the second interest points have been determined at step 1510, the process 1500 can move to step 1512 wherein the distance and direction of movement of the camera between the first captured image and second captured image can be determined in substantially the same manner as described above with respect to step 1414 of FIG. 14. Thus, the interest points of the first and second captured images can be matched to one another (for instance by using a KNN matching algorithm) and the movement of the matched points can be determined using homography to determine the amount and direction of movement of the camera.

Once the extent and direction of camera movement have been determined at step 1512, the process 1500 can move to step 1514 wherein the first and second captured images are combined to form a third image based on the determined distance and direction of the camera movement as determined at step 1512. For instance, if the camera has moved down and to the left between the capture of the first frame and the capture of the second frame, then the second image can be stitched to the first image such that the field of view of the second image appears down and to the left of the first image's field of view when combining the two images to form the third image. In other words, the point or points at which the two images are stitched together is commensurate with the camera movement that took place between when the two images were captured. In this way, the viewer of the combined image can be sure that the combined image accurately reflects the anatomy of the user.

Once the images have been combined at step 1514, the process 1500 can move to step 1516 wherein depth information for the third image can be acquired. The depth information for the composite third image can be acquired from the depth information of the first image and the depth image of the second image. The depth information for each captured frame of the video data can be acquired using the systems and methods described above with respect to FIG. 3, and specifically step 306. Thus, the depth information for each captured frame can be acquired using the structure from motion, time of flight sensor, or other methods described above to acquire three-dimensional depth information from a plurality of images acquired from a medical imaging device. As described above, by tracking the motion of the camera between frames, the systems and methods described above are able to generate a three-dimensional model of the patient's anatomy that can be used in many procedures and applications to give the user a more holistic view of the internal portion of the patient's body. Using motion tracking to stitch three-dimensional images together can allow for a large scale three-dimensional model to be built progressively throughout the medical procedure. The three-dimensional model generated using the methods described above can be colored and textured using the pixel (i.e., RGB) data for the images. The three-dimensional model can be generated automatically, or its creation can be triggered by a user or a hybrid of both automatic and surgeon triggered. Allowing for a user to trigger creation of a three-dimensional model can allow for multiple models to be created, for instance to show differences in the anatomy prior to the surgery and after the surgery.

The three-dimensional model generated using the process described above, or another external three-dimensional model, can be used to generate graphical overlays on two-dimensional images produced by a medical imaging device in order to give the user an augmented reality view of the surgical space to help them visualize phenomenon in the surgical space that may not otherwise be possible two view on the raw two-dimensional video data being generated by the medical imaging device. As described in further detail below, a three-dimensional model like the one described above, could allow for the user to visualize three-dimensional aspects of the two-dimensional image shown on a display. For instance, using a three-dimensional model of the anatomy of the patient, a heat map can be overlaid on a two-dimensional image to show bur depth (for instance in a hip procedure) thereby giving the user a guide as to the depth of the anatomy shown in a two-dimensional image.

Figure 16:
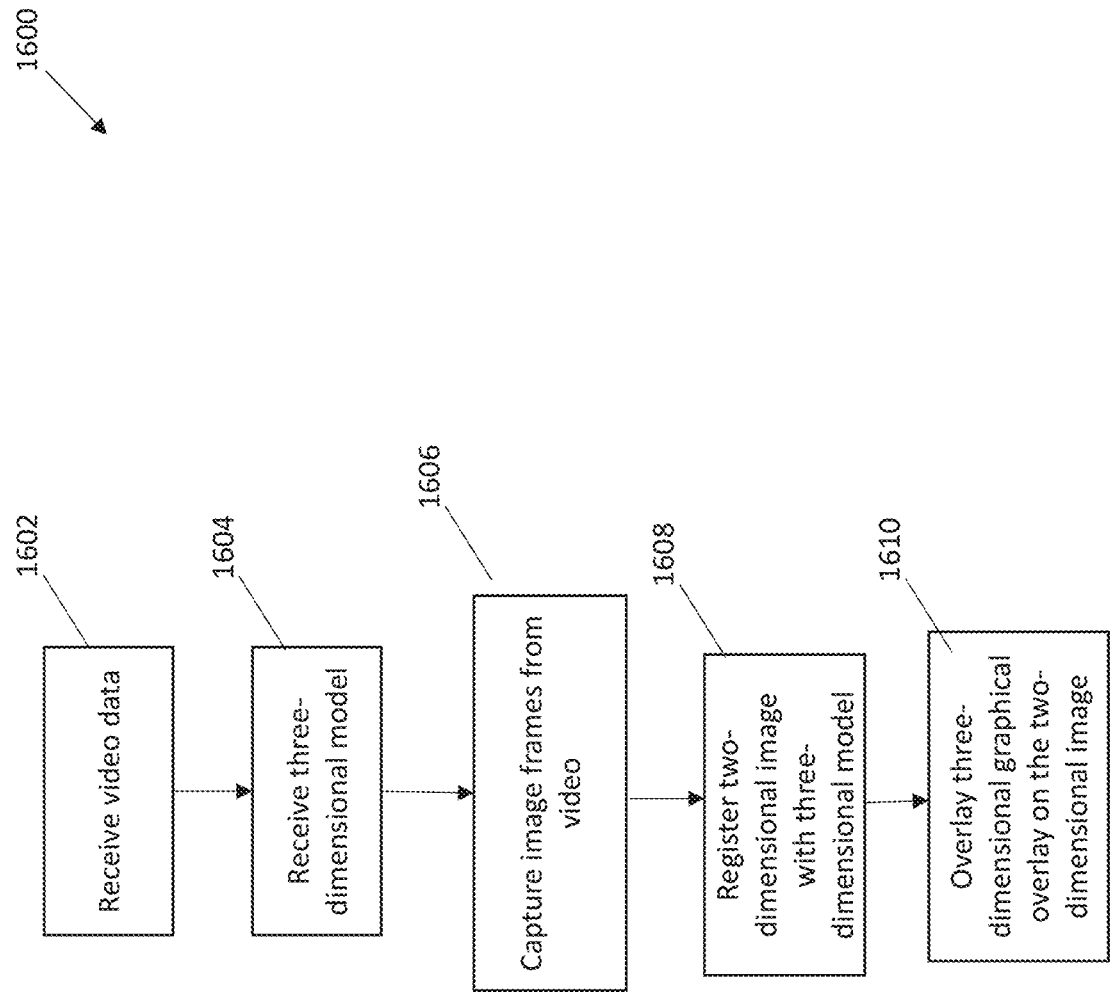
FIG. 16 illustrates an exemplary process for generating a three-dimensional overlay on one or more two-dimensional images according to examples of the disclosure.

FIG. 16 illustrates an exemplary process for generating a three-dimensional overlay on one or more two-dimensional images according to examples of the disclosure. The process 1600 of FIG. 16 can begin at step 1602 wherein video data is received from a medical imaging device. The process of receiving the video data can be substantially similar to the processes for receiving video data described above with respect to FIGS. 3, 6, 7, 14, and 15, and thus a discussion of those figures can be referenced for details on how video is received at step 1602 of FIG. 16. Once the video data has been received at step 1604, the process 1600 can move to step 1604 wherein a three-dimensional model of the anatomy shown in the video data is received. The three-dimensional model can be generated using the process described above with respect to FIG. 15. Additionally, or alternatively, the three-dimensional model can be generated using other methods such as from a pre-operative computerized tomography (CT) scan or a magnetic resonance imaging (MM) scan. Additionally or alternatively, the three-dimensional model received at step 1604 can be received from a database that stores a variety of three-dimensional models of different features of the human body. For instance, the Stryker Orthopedic Modeling and Analytics (SOMA) utilizes a comprehensive database of CT-scans, and three-dimensional bone models which can be utilized as the three-dimensional models received at step 1604. Once the three-dimensional model is received at step 1604, the process 1600 can move to step 1606 wherein one or more two dimensional images are captured from the video data received at 1602. The one or more frames of data can be captured using the methods for capturing two-dimensional frames or images from video data described above with respect to FIGS. 3, 6, 7, 14, and 15. Once the one or more two-dimensional images are acquired at step 1606, the process 1600 can move to step 1608 wherein a two-dimensional image captured from the received video data is registered with the three-dimensional model received at step 1602. The "registering" of a two-dimensional image with a three-dimensional model can refer to the process of placing the image and the three-dimensional on the same coordinate system, such that the three-dimensional model and the two-dimensional image can be aligned in space. For instance if a two-dimensional image and the three-dimensional model both show a certain feature, then registering the two-dimensional image to the three-dimensional image can include aligning the two so that the common features are aligned with one another in space. Registration can be implemented using a variety of techniques such as electromagnetic (EM) tracking, through the use of fiducials in both the two-dimensional image and three-dimensional model, multi-model registration (e.g., matching segmented structures from CT/MR scans and scope frame, etc.).

The registration of step 1608 can be an ongoing process since the camera used to capture the video data received at step 1602 may be in motion and thus the registration process may be conducted periodically to realign the three-dimensional model with the two-dimensional image. The realignment can be implemented using the processes described above with respect to FIGS. 14 and 15 for tracking the amount and direction of motion of a camera, and specifically the process described with respect to steps 1408-1414 of FIG. 14, and steps 1504-1512 of FIG. 15. Motion tracking can also be implemented using IMU sensor data, EM tracking, or some combination of the techniques described above. Once a two-dimensional image is registered with the three-dimensional model at step 1608, the process 1600 can move to step 1610 wherein a three-dimensional graphical overlay is overlaid on the two-dimensional image.

The graphical overlays described above with respect to step 1608 can include one or more drill trajectory overlays. A drill trajectory graphical overlay can allow the user to visualize various aspects of the drilling process such as the projected current drill trajectory, an optimal drill trajectory for a given procedure, a preplanned drill trajectory, various drill width options, drill placement guides, and the expected strength of current graft placed along a drill trajectory. A two-dimensional image from the video data can be registered to one or more of the of three-dimensional models described above with respect to FIG. 16 and the one or more three-dimensional models can be referenced to create one or more graphical overlays that help the user to plan a drilling procedure as described above. For instance, the one or more three-dimensional models registered with a two-dimensional image can aid the user in avoiding underlying anatomical structures such as bone or tissue when drilling even though the bone or tissue may not be visible in the two-dimensional image.

Additionally or alternatively to using a three dimensional model to generate graphical overlays on images taken by a medical imaging device, in one or more examples, the three dimensional model and measurements taken using the three-dimensional model within the internal area of the patient, can be used to aid a user in generating and cutting graft pieces that can then be grafted into the internal area of the patient. If the user is using the three-dimensional measuring capabilities of the system described above to measure the length of an area to be grafted, the user may still be required to use a ruler or other measuring device to ensure the graft that they cut for placement into the patient matches the measurement taken within the internal area of the patient. This process thus could introduce human error, and overall may be inefficient to ensuring that a graft cut (on a back table in the surgical table) is of the right size to match the area within the patient where a graft is needed. Thus, in order to minimize human error, in one or more examples, measurements generated within the internal area of a patient using the systems and methods described above can be used to generate a projection onto a back table in the surgical theatre onto a piece of graft material, so that the surgeon can accurately cut the graft portion from the material according to a measurement taken within the internal area of the patient using endoscopic imaging data.

Figure 17:
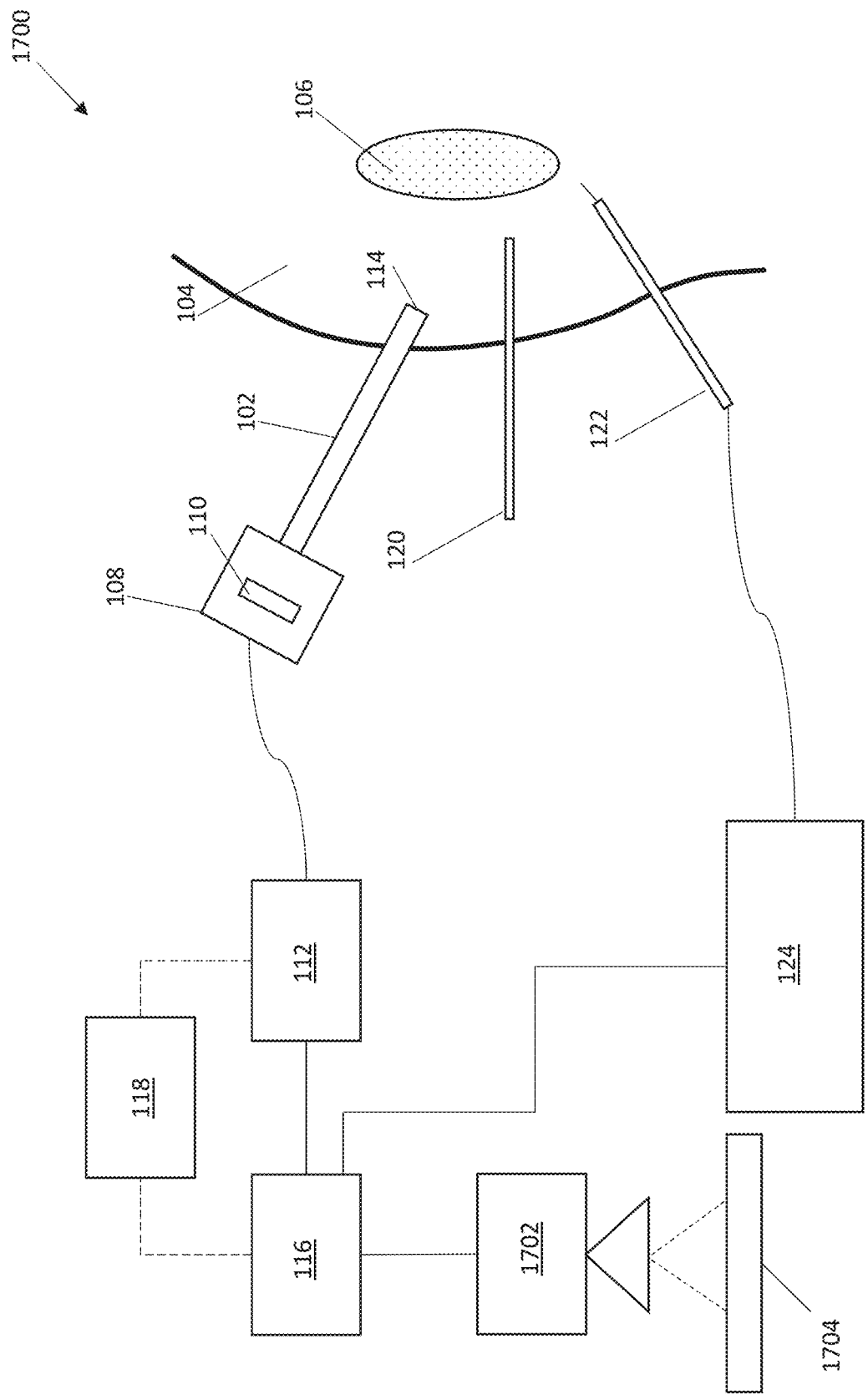
FIG. 17 illustrates an exemplary graft projection system according to examples of the disclosure.

FIG. 17 illustrates an exemplary graft projection system according to examples of the disclosure. In one or more examples, the example system 1700 can be similar to the exemplary endoscopy system 100 described above with respect to FIG. 1. Thus, the system 1700 can include substantially the same components included in system 100 of FIG. 1 including an endoscope 102, an endoscopic camera head 108, one or more imaging sensors 110, a camera control unit 112, an imaging processing unit 116, and one or more displays 118. Thus, for a detailed discussion of the operation of those components, the discussion above with respect to those components and made with respect to FIG. 1 can be referenced.

The system 1700 in addition to the components that are the same as the system 100 of FIG. 1 described above, can also include a projector 1702 that can be positioned above a back table 1704 and can be configured to project measurements determined by image processing unit 116 onto a graft material laid out on back table 1704, so that a surgeon can cut the graft material to the precise measurements taken from the endoscopic imaging data according to systems and methods described above. In order to ensure that the projection generates size accurate projections, the projector 1702 can be placed at a pre-determined height above the back table 1704. Additionally or alternatively, the projector 1702 can be provided with the distance to the back table 1704 (or the position of the back table 1704 relative to the projector 1702), and the projector 1702 can determine the settings required to project a measurement onto the back table 1702 so as to generate size accurate projections. The projector 1702 can be communicatively coupled to the image processing unit 116. Thus, any measurements determined by the imaging processing unit 116 using the methods described above, can be communicated to the projector 1702 so that the projector can project (in actual size) the size and shape of the graft piece to be cut from the graft material onto the graft material. In this way, the surgeon preparing a graft piece, does not have to replicate the measurement determined by imaging processing unit 116 to cut a graft, but instead can have the graft piece projected onto the graft material, so that the surgeon can simply follow the contours of the graft piece projected onto the graft material to cut an accurate graft piece.

The projector can be especially useful in situations in which grafts are not simple geometric shapes (i.e., circle, square, line) but instead are complex geometric shapes. For instance, cartilage defects are often shaped in unconventional geometries. Conventionally, in order to generate accurate grafts for cartilage defects, the defect in the internal portion can be further cut so as to resemble a traditional shape such as a circle, thus making cutting a graft piece from graft material easier. However, using the projection system 1700 described above, the geometry of a cartilage defect can be directly projected onto the graft material (sitting on the back table 1704) so that the surgeon can simply carve the graft from the material using the contours of the projection. The graft can include allograft or autograft material. Additionally or alternatively, the graft material can be synthetic. The graft can include ligaments, vessels, in addition to cartilage grafts as described above.

Referring back to the discussion above with respect to FIG. 3, and specifically to the use of AruCo markers to acquire fiducial information (see step 308), the image processing unit being used to detect the presence of ArUco markers in the imaging data may need to be calibrated to ensure that any warping or other visual artifacts introduced by the imaging device does not cause errors when detecting ArUco markers.

Figure 18:
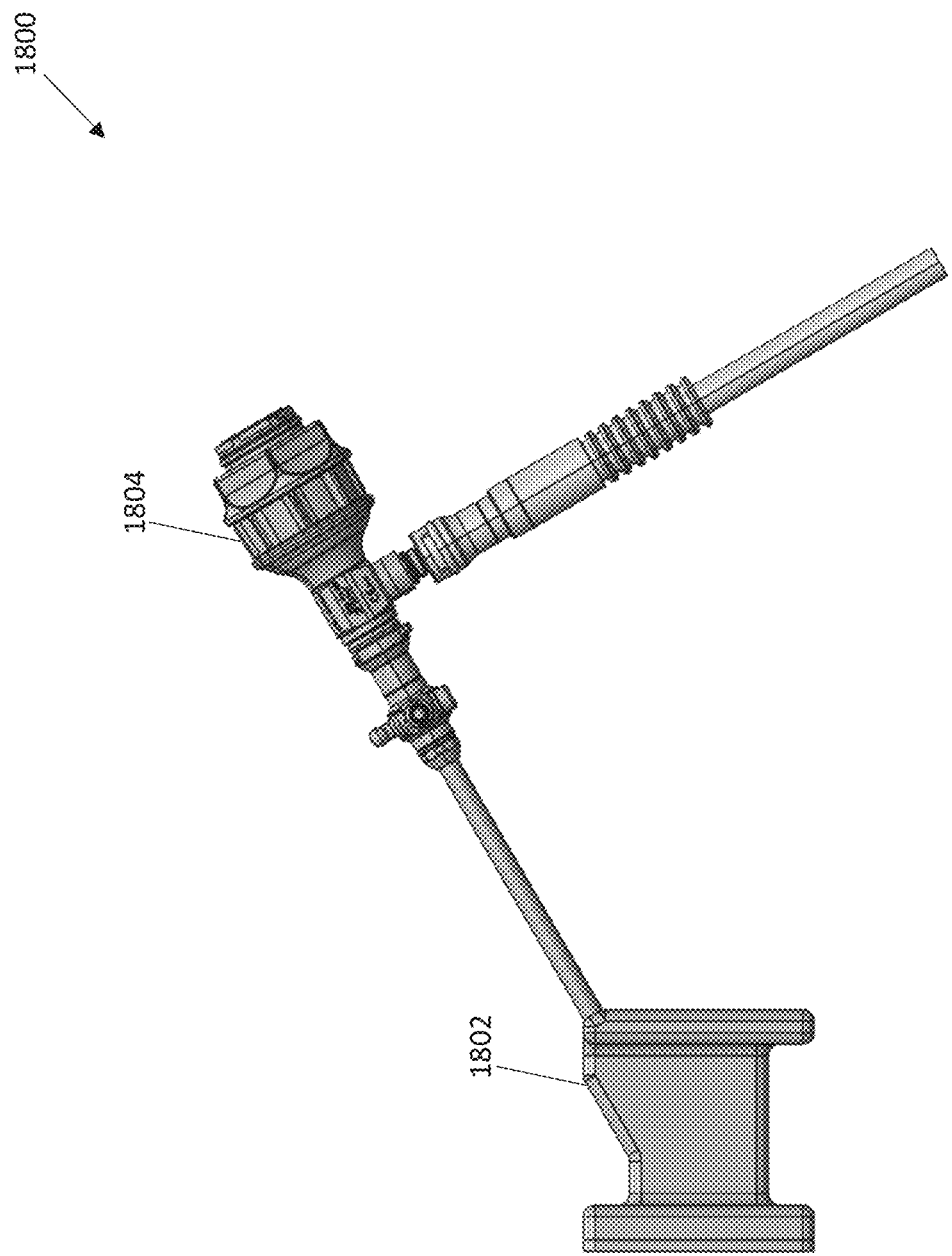
FIG. 18 illustrates an exemplary fiducial marker calibration device according to examples of the disclosure.

FIG. 18 illustrates an exemplary fiducial marker calibration device according to examples of the disclosure. While the discussion of the calibration device 1800 uses ArUco markers as an example, the example should not be seen as limiting, and the device 1800 of FIG. 18 can be applied to other fiducial markers such as AprilTags. The calibration device 1800 can include a chamber 1802 and an imaging device interface 1804. The imaging device interface can be configured to receive an imaging device, and position the imaging device so that the imaging device can view the internal area of the chamber 1802.

The chamber 1802 can include one or more test ArUco markers that are disposed within the chamber and are positioned within the chamber such that they can be viewed by an imaging device that is connected to the device 1800 by the imaging device interface 1804. The chamber 1802 can be filled with a liquid (i.e., saline) so as to recreate the environment of the internal area of a patient. The test ArUco markers in the chamber can be viewed by the imaging device (when the chamber is filled with fluid) to determine an image correction factor that should be applied to images taken by the imaging device when determining the size and position of ArUco markers that appear in an image taken during a surgical procedure. For instance, the test ArUco markers can be of a size and position that is known ahead of time. Thus, when viewing the test ArUco markers using an imaging device, if the determined size and location of the ArUco markers (as determined by an imaging processing unit attached to the imaging device) does not match the known size and position of the markers in the chamber 1802, then the imaging processing unit can apply a correction factor (that it can then apply to all subsequent ArUco markers images) so as to "calibrate" the imaging device. In one or more examples, the calibration of an imaging device to detect ArUco markers can be performed without saline or other liquids. For instance, in one or more examples, a calibration card with an array of ArUco markers can be used (with the card being placed in a plain air environment.) In one or more examples, the calibration information can be mathematically altered to account for the difference in refractive index between air and saline (or other liquid).

The systems and methods described above can be implemented in a variety of computing environments. For instance, the processing of images to generate three-dimensional models and to generate three-dimensional measurement can be performed on a computing device that is located in a surgical theater where the, e.g. surgical, procedure is performed. Locating the surgical device in the surgical theater can avoid having to transmit sensitive patient data (such as the endoscopic data) across a computing network wherein the data could be vulnerable to being acquired by a malicious actor or other entity who does not have authorization to access the data. Additionally or alternatively, the processing of images can be performed on a cloud-based computing device that is not located in the surgical theater, in which case the images and data associated with generating three-dimensional measurements can be transmitted to the cloud-based computing device for processing, and the results can be transmitted back to the surgical theater by the cloud-based computing device.

Figure 19:
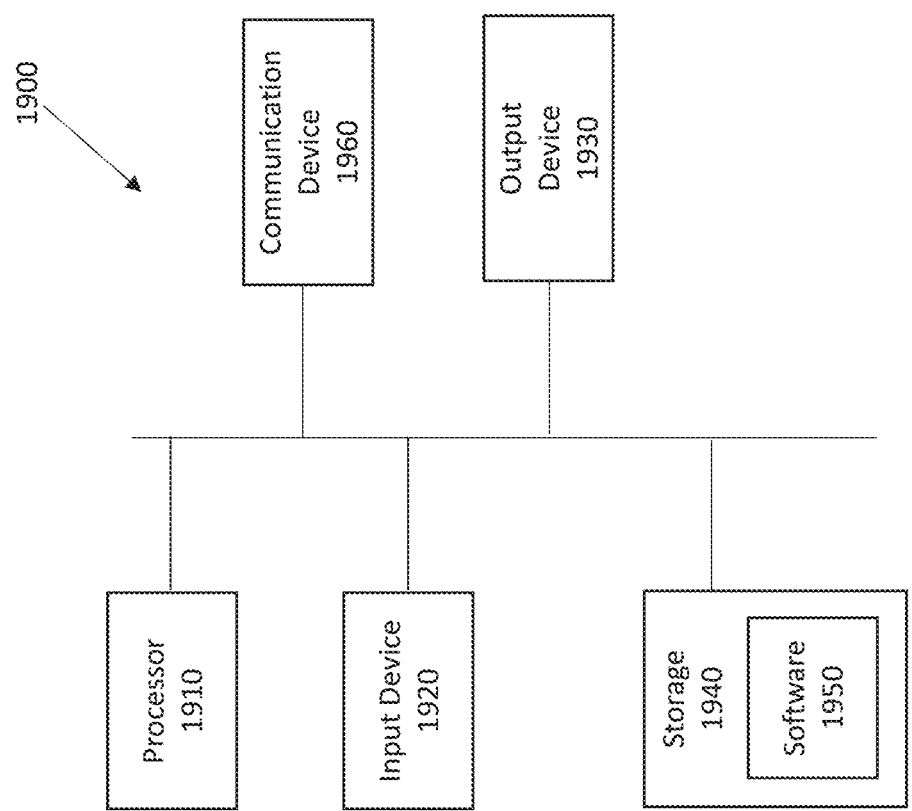
FIG. 19 illustrates an exemplary computing system, according to examples of the disclosure.

FIG. 19 illustrates an example of a computing system 1900, in accordance with some embodiments, that can be used for one or more of components of system 100 of FIG. 1, such as one or more of camera head 108, camera control unit 112, and image processing unit 118. System 1900 can be a computer connected to a network, such as one or more networks of hospital, including a local area network within a room of a medical facility and a network linking different portions of the medical facility. System 1900 can be a client or a server. As shown in FIG. 19, system 1900 can be any suitable type of processor-based system, such as a personal computer, workstation, server, handheld computing device (portable electronic device) such as a phone or tablet, or dedicated device. The system 1900 can include, for example, one or more of input device 1920, output device 1930, one or more processors 1910, storage 1940, and communication device 1960. Input device 1920 and output device 1930 can generally correspond to those described above and can either be connectable or integrated with the computer.

Input device 1920 can be any suitable device that provides input, such as a touch screen, keyboard or keypad, mouse, gesture recognition component of a virtual/augmented reality system, or voice-recognition device. Output device 1930 can be or include any suitable device that provides output, such as a display, touch screen, haptics device, virtual/augmented reality display, or speaker.

Storage 1940 can be any suitable device that provides storage, such as an electrical, magnetic, or optical memory including a RAM, cache, hard drive, removable storage disk, or other non-transitory computer readable medium. Communication device 1960 can include any suitable device capable of transmitting and receiving signals over a network, such as a network interface chip or device. The components of the computing system 1900 can be connected in any suitable manner, such as via a physical bus or wirelessly.

Processor(s) 1910 can be any suitable processor or combination of processors, including any of, or any combination of, a central processing unit (CPU), field programmable gate array (FPGA), and application-specific integrated circuit (ASIC). Software 1950, which can be stored in storage 1940 and executed by one or more processors 1910, can include, for example, the programming that embodies the functionality or portions of the functionality of the present disclosure (e.g., as embodied in the devices as described above)

Software 1950 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1940, that can contain or store programming for use by or in connection with an instruction execution system, apparatus, or device.

Software 1950 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

System 1900 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 1900 can implement any operating system suitable for operating on the network. Software 1950 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated. For the purpose of clarity and a concise description, features are described herein as part of the same or separate embodiments; however, it will be appreciated that the scope of the disclosure includes embodiments having combinations of all or some of the features described.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. A method for measuring three-dimensional distances using endoscopic images, the method comprising:
    receiving video data captured from an endoscopic imaging device configured to image an internal area of a patient;
    capturing one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both;
    generating a three-dimensional model of the internal area based on the captured one or more two-dimensional images;
    determining a size of a three-dimensional area of the three-dimensional model based on the one or more fiducial markers of the object configured to indicate the pre-determined dimension;
    identifying a first point on the one or more two-dimensional images;

identifying a second point on the one or more two-dimensional images; and determining a three-dimensional measurement between the first point and the second point in the area based on the determined size of the three-dimensional area and the generated three-dimensional model of the area.

2. The method of claim 1, wherein capturing the one or more two-dimensional images comprises:

in response to a user requesting a measurement, receiving a first indication to mark a start time point in the received video data;

receiving a second indication to mark a stop time point in the received video data;

extracting a first two-dimensional image corresponding to the first indication; and extracting a second two-dimensional image corresponding to the second indication.

3. The method of claim 1, wherein capturing the one or more two-dimensional images comprises:

receiving a first indication at a graphical user interface on a computing device display;

receiving a second indication at the graphical user interface on the computing device display;

extracting a first two-dimensional image corresponding to the first indication; and extracting a second two-dimensional image corresponding to the second indication.

4. The method of claim 1, wherein capturing the one or more two-dimensional images comprises:

capturing a first image with the endoscopic imaging device located at a first position in the area; and capturing a second image with the imaging device located at a second position in the area.

5. The method of claim 4, wherein generating a three-dimensional model of the area based on the captured one or more two-dimensional images comprises applying a structure-from-motion procedure to the first and second images to generate the three-dimensional model of the area.

6. The method of claim 1, wherein generating a three-dimensional model of the area based on the captured one or more two-dimensional images comprises:

capturing a first two-dimensional image of the area;

receiving data from a time-of-flight sensor, wherein the received data corresponds to the imaged area; and generating the three-dimensional model of the area based on the captured first two-dimensional image of the area and the received data from the time-of-flight sensor.

7. The method of claim 1, wherein the endoscopic imaging device comprises a stereo camera, and wherein capturing the one or more two-dimensional images comprises capturing a first two-dimensional image and a second two-dimensional image using the stereo camera of the endoscopic imaging device.

8. The method of claim 7, wherein generating a three-dimensional model of the area based on the captured one or more two-dimensional images comprises applying a structure-from-motion procedure to the first and second two-dimensional images to generate the three-dimensional model of the area.

9. The method of claim 1, wherein identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

10. The method of claim 9, wherein segmenting the object from the first and second images of the one or more two-dimensional images comprises applying one or more machine learning models to the first and second images, wherein the one or more machine learning models are created using a supervised training process that comprises using one or more annotated images to train the machine learning model.

11. The method of claim 1, wherein determining a three-dimensional measurement between the first point and the second point in the area based on the determined size of the area and the generated three-dimensional model of the area comprises determining a distance along a surface between the first position and the second position.

12. The method of claim 1, wherein determining a three-dimensional measurement between the first point and the second point in the area based on the determined size of the area and the generated three-dimensional model of the area comprises determining the point-to-point distance between the first position and the second position.

13. A system for measuring three-dimensional distances using endoscopic images, the system comprising:

a memory;

one or more processors;

wherein the memory stores one or more programs that when executed by the one or more processors, cause the one or more processors to:

receive video data captured from an endoscopic imaging device configured to image an internal area of a patient;

capture one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both;

generate a three-dimensional model of the internal area based on the captured one or more two-dimensional images;

determine a size of a three-dimensional area of the three-dimensional model based on the one or more fiducial markers of the object configured to indicate the pre-determined dimension;

identify a first point on the one or more two-dimensional images;

identify a second point on the one or more two-dimensional images; and determine a three-dimensional measurement between the first point and the second point in the area based on the determined size of the three-dimensional area and the generated three-dimensional model of the area.

14. The system of claim 13, wherein capturing the one or more two-dimensional images comprises:

in response to a user requesting a measurement, receiving a first indication to mark a start time point in the received video data;

receiving a second indication to mark a stop time point in the received video data;

extracting a first two-dimensional image corresponding to the first indication; and extracting a second two-dimensional image corresponding to the second indication.

15. The system of claim 13, wherein capturing the one or more two-dimensional images comprises:

receiving a first indication at a graphical user interface on a computing device display;

receiving a second indication at the graphical user interface on the computing device display;

extracting a first two-dimensional image corresponding to the first indication; and extracting a second two-dimensional image corresponding to the second indication.

16. The system of claim 13, wherein capturing the one or more two-dimensional images comprises:

capturing a first image with the endoscopic imaging device located at a first position in the area; and capturing a second image with the imaging device located at a second position in the area.

17. The system of claim 16, wherein generating a three-dimensional model of the area based on the captured one or more two-dimensional images comprises applying a structure-from-motion procedure to the first and second images to generate the three-dimensional model of the area.

18. The system of claim 13, wherein generating a three-dimensional model of the area based on the captured one or more two-dimensional images comprises:

capturing a first two-dimensional image of the area;

receiving data from a time-of-flight sensor, wherein the received data corresponds to the imaged area; and generating the three-dimensional model of the area based on the captured first two-dimensional image of the area and the received data from the time-of-flight sensor.

19. The system of claim 13, wherein the endoscopic imaging device comprises a stereo camera, and wherein capturing the one or more two-dimensional images comprises capturing a first two-dimensional image and a second two-dimensional image using the stereo camera of the endoscopic imaging device.

20. The system of claim 19, wherein generating a three-dimensional model of the area based on the captured one or more two-dimensional images comprises applying a structure-from-motion procedure to the first and second two-dimensional images to generate the three-dimensional model of the area.

21. The system of claim 13, wherein identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

22. The system of claim 21, wherein segmenting the object from the first and second images of the one or more two-dimensional images comprises applying one or more machine learning models to the first and second images, wherein the one or more machine learning models are created using a supervised training process that comprises using one or more annotated images to train the machine learning model.

23. The system of claim 13, wherein determining a three-dimensional measurement between the first point and the second point in the area based on the determined size of the area and the generated three-dimensional model of the area comprises determining a distance along a surface between the first position and the second position.

24. The system of claim 13, wherein determining a three-dimensional measurement between the first point and the second point in the area based on the determined size of the area and the generated three-dimensional model of the area comprises determining the point-to-point distance between the first position and the second position.

25. A non-transitory computer readable storage medium storing one or more programs for measuring three-dimensional distances, for execution by one or more processors of an electronic device that when executed by the device, cause the device to:

receive video data captured from an endoscopic imaging device configured to image an internal area of a patient;

capture one or more two-dimensional images of the internal area from the received video data, wherein an image of the one or more two-dimensional images comprises a visualization of an object, and wherein the object comprises one or more fiducial markers configured to indicate a pre-determined dimension of the object or the fiducial marker, or both;

generate a three-dimensional model of the internal area based on the captured one or more two-dimensional images;

determine a size of a three-dimensional area of the three-dimensional model based on the one or more fiducial markers of the object configured to indicate the pre-determined dimension;

identify a first point on the one or more two-dimensional images;

identify a second point on the one or more two-dimensional images; and determine a three-dimensional measurement between the first point and the second point in the area based on the determined size of the three-dimensional area and the generated three-dimensional model of the area.

26. The non-transitory computer readable storage medium of claim 25, wherein capturing the one or more two-dimensional images comprises:

in response to a user requesting a measurement, receiving a first indication to mark a start time point in the received video data;

receiving a second indication to mark a stop time point in the received video data;

extracting a first two-dimensional image corresponding to the first indication; and extracting a second two-dimensional image corresponding to the second indication.

27. The non-transitory computer readable storage medium of claim 25, wherein capturing the one or more two-dimensional images comprises:

receiving a first indication at a graphical user interface on a computing device display;

receiving a second indication at the graphical user interface on the computing device display;

extracting a first two-dimensional image corresponding to the first indication; and extracting a second two-dimensional image corresponding to the second indication.

28. The non-transitory computer readable storage medium of claim 25, wherein capturing the one or more two-dimensional images comprises:

capturing a first image with the endoscopic imaging device located at a first position in the area; and capturing a second image with the imaging device located at a second position in the area.

29. The non-transitory computer readable storage medium of claim 28, wherein generating a three-dimensional model of the area based on the captured one or more two-dimensional images comprises applying a structure-from-motion procedure to the first and second images to generate the three-dimensional model of the area.

30. The non-transitory computer readable storage medium of claim 25, wherein generating a three-dimensional model of the area based on the captured one or more two-dimensional images comprises:

capturing a first two-dimensional image of the area;
receiving data from a time-of-flight sensor, wherein the received data corresponds to the imaged area; and
generating the three-dimensional model of the area based on the captured first two-dimensional image of the area and the received data from the time-of-flight sensor.

31. The non-transitory computer readable storage medium of claim 25, wherein the endoscopic imaging device comprises a stereo camera, and wherein capturing the one or more two-dimensional images comprises capturing a first two-dimensional image and a second two-dimensional image using the stereo camera of the endoscopic imaging device.

32. The non-transitory computer readable storage medium of claim 31, wherein generating a three-dimensional model of the area based on the captured one or more two-dimensional images comprises applying a structure-from-motion procedure to the first and second two-dimensional images to generate the three-dimensional model of the area.

33. The non-transitory computer readable storage medium of claim 25, wherein identifying the first point on the one or more two-dimensional images comprises segmenting the object from the first image of the one or more two-dimensional images, and wherein identifying the second point on the one or more two-dimensional images comprises segmenting the object from the second image of the one or more two-dimensional images.

34. The non-transitory computer readable storage medium of claim 33, wherein segmenting the object from the first and second images of the one or more two-dimensional images comprises applying one or more machine learning models to the first and second images, wherein the one or more machine learning models are created using a supervised training process that comprises using one or more annotated images to train the machine learning model.

35. The non-transitory computer readable storage medium of claim 25, wherein determining a three-dimensional measurement between the first point and the second point in the area based on the determined size of the area and the generated three-dimensional model of the area comprises determining a distance along a surface between the first position and the second position.

36. The non-transitory computer readable storage medium of claim 25, wherein determining a three-dimensional measurement between the first point and the second point in the area based on the determined size of the area and the generated three-dimensional model of the area comprises determining the point-to-point distance between the first position and the second position.

* * * * *